US011660386B2

(12) United States Patent
Shubinsky et al.

(10) Patent No.: US 11,660,386 B2
(45) Date of Patent: May 30, 2023

(54) DISPOSABLE INFUSION FLUID DELIVERY DEVICE FOR PROGRAMMABLE LARGE VOLUME DRUG DELIVERY

(71) Applicant: ICU Medical, Inc., San Clemente, CA (US)

(72) Inventors: Gary David Shubinsky, Buffalo Grove, IL (US); Thomas D. Johnson, Gurnee, IL (US); Jeffrey Donald Merwin, Lincolnshire, IL (US); Vlad Radu Balteanu, Lake Bluff, IL (US)

(73) Assignee: ICU Medical, Inc., San Clemente, CA (US)

( * ) Notice: Subject to any disclaimer, the term of this patent is extended or adjusted under 35 U.S.C. 154(b) by 130 days.

(21) Appl. No.: 17/142,823

(22) Filed: Jan. 6, 2021

(65) Prior Publication Data
US 2021/0202059 A1 Jul. 1, 2021

Related U.S. Application Data

(62) Division of application No. 15/164,277, filed on May 25, 2016, now Pat. No. 10,918,787.
(Continued)

(51) Int. Cl.
A61M 5/142 (2006.01)
A61M 5/172 (2006.01)
A61M 5/14 (2006.01)

(52) U.S. Cl.
CPC .......... *A61M 5/142* (2013.01); *A61M 5/1413* (2013.01); *A61M 5/172* (2013.01);
(Continued)

(58) Field of Classification Search
CPC .......... A61M 2205/18; A61M 2205/33; A61M 2205/3327; A61M 2205/3331;
(Continued)

(56) References Cited

U.S. PATENT DOCUMENTS

| 790,353 A | 5/1905 | Estlingen |
| 1,248,058 A | 11/1917 | Bailey |

(Continued)

FOREIGN PATENT DOCUMENTS

| CA | 2 808 379 | 2/2012 |
| CN | 304975990 S | 1/2019 |

(Continued)

OTHER PUBLICATIONS

"CritiCore® Monitor: Critical Fluid Output and Core Bladder Temperature Monitor", BARD Urological Catheter Systems, Advertisement, 2005, pp. 2.
(Continued)

*Primary Examiner* — Shefali D Patel
(74) *Attorney, Agent, or Firm* — Knobbe, Martens, Olson & Bear, LLP

(57) ABSTRACT

A disposable electronically controlled infusion pump system includes at least one disposable infusion container and at least one disposable electronically controlled medication pumping system. The at least one disposable infusion container is configured to contain infusion fluid. The at least one disposable electronically controlled medication pumping system is fluidly connected to the at least one disposable infusion container. The at least one disposable electronically controlled medication pumping system includes an infusion channel, a disposable electronically controlled micropump, and valves, but may further include a microprocessor, a memory, a battery or a power receiver configured to wirelessly receive power, a wireless communication device, and other components. The memory is in electronic communication with the microprocessor. The wireless communication device is configured to receive a wireless signal which wirelessly controls the at least one disposable electronically controlled medication pumping system. The disposable elec-
(Continued)

tronically controlled micropump is configured to pump the infusion fluid through the infusion channel. The valves are connected to the infusion channel.

20 Claims, 7 Drawing Sheets

Related U.S. Application Data

(60) Provisional application No. 62/166,422, filed on May 26, 2015.

(52) U.S. Cl.
CPC ............... *A61M 2205/3331* (2013.01); *A61M 2205/3368* (2013.01); *A61M 2205/3576* (2013.01); *A61M 2205/50* (2013.01); *A61M 2205/52* (2013.01); *A61M 2205/6072* (2013.01)

(58) Field of Classification Search
CPC .. A61M 2205/3334; A61M 2205/3368; A61M 2205/3379; A61M 2205/3576; A61M 2205/50; A61M 2205/502; A61M 2205/52; A61M 2205/6009; A61M 2205/6072; A61M 2205/8206; A61M 2205/8262; A61M 5/14; A61M 5/1413; A61M 5/142; A61M 5/172

See application file for complete search history.

(56) References Cited

U.S. PATENT DOCUMENTS

| | | |
|---|---|---|
| 1,576,445 A | 3/1926 | Mitchell |
| 1,647,039 A | 4/1927 | Fischer |
| 1,749,491 A | 4/1930 | Kokay |
| 2,820,886 A | 5/1955 | Posey |
| 2,869,690 A | 1/1959 | Winters et al. |
| 2,903,165 A | 9/1959 | Hanson et al. |
| 3,185,153 A | 5/1965 | Leucci |
| 3,316,935 A | 5/1967 | Kaiser et al. |
| 3,367,270 A | 2/1968 | Schlosser |
| 3,427,986 A | 2/1969 | Corneil |
| 3,606,596 A | 9/1971 | Edwards |
| 3,647,176 A | 3/1972 | Usry |
| 3,650,296 A | 3/1972 | Johnson et al. |
| 3,771,862 A | 11/1973 | Land et al. |
| 3,777,581 A | 12/1973 | Sartori |
| 3,812,482 A | 5/1974 | Clark |
| 3,898,637 A | 8/1975 | Wolstenholme |
| 3,901,231 A | 8/1975 | Olson |
| 3,913,384 A | 10/1975 | Furuya |
| 3,921,622 A | 11/1975 | Cole |
| 3,935,876 A | 2/1976 | Massie et al. |
| 3,985,133 A | 10/1976 | Jenkins et al. |
| 4,068,521 A | 1/1978 | Cosentino et al. |
| 4,155,362 A | 5/1979 | Jess |
| 4,187,057 A | 2/1980 | Xanthopoulos |
| 4,193,635 A | 3/1980 | Thiruvengadam et al. |
| 4,195,515 A | 4/1980 | Smoll |
| 4,211,380 A | 7/1980 | Lillegard et al. |
| 4,213,454 A | 7/1980 | Shim |
| 4,223,813 A | 9/1980 | Garrett et al. |
| 4,236,880 A | 12/1980 | Archibald |
| 4,240,294 A | 12/1980 | Grande |
| 4,244,365 A | 1/1981 | McGill |
| 4,261,356 A | 4/1981 | Turner et al. |
| 4,291,701 A | 9/1981 | Bowman et al. |
| 4,303,376 A | 12/1981 | Siekmann |
| 4,332,378 A | 6/1982 | Pryor |
| 4,343,316 A | 8/1982 | Jespersen |
| 4,381,591 A | 5/1983 | Barger et al. |
| 4,397,642 A | 8/1983 | Lamadrid |
| 4,397,648 A | 8/1983 | Knute et al. |
| 4,406,042 A | 9/1983 | McPhee et al. |
| 4,418,565 A | 12/1983 | St. John |
| 4,439,179 A | 3/1984 | Lueders et al. |
| 4,468,222 A | 8/1984 | Lundquist |
| 4,469,765 A | 9/1984 | McCartney et al. |
| 4,482,347 A | 11/1984 | Borsanyi |
| 4,496,351 A | 1/1985 | Hillel et al. |
| 4,513,885 A | 4/1985 | Hogan |
| 4,528,847 A | 7/1985 | Halmi |
| 4,530,647 A | 7/1985 | Uno |
| 4,551,134 A | 11/1985 | Slavik et al. |
| 4,565,500 A | 1/1986 | Jeensalute et al. |
| 4,573,968 A | 3/1986 | Parker |
| 4,585,441 A | 4/1986 | Archibald et al. |
| 4,586,691 A | 5/1986 | Kozlow |
| 4,589,171 A | 5/1986 | McGill et al. |
| 4,607,520 A | 8/1986 | Dam |
| 4,613,325 A | 9/1986 | Abrams |
| 4,626,243 A | 12/1986 | Singh et al. |
| 4,626,244 A | 12/1986 | Reinicke |
| 4,644,960 A | 2/1987 | Johans |
| 4,680,977 A | 7/1987 | Conero et al. |
| 4,681,563 A | 7/1987 | Deckert et al. |
| 4,683,916 A | 8/1987 | Raines |
| 4,689,043 A | 8/1987 | Bisha |
| 4,694,273 A | 9/1987 | Franchino |
| 4,696,671 A | 9/1987 | Epstein et al. |
| 4,722,725 A | 2/1988 | Sawyer |
| 4,728,265 A | 3/1988 | Cannon |
| 4,735,558 A | 4/1988 | Kienholz et al. |
| 4,756,706 A | 7/1988 | Kerns et al. |
| 4,758,228 A | 7/1988 | Williams |
| 4,759,749 A | 7/1988 | Verkaart |
| 4,802,650 A | 2/1989 | Stricker |
| 4,811,928 A | 3/1989 | Iwatschenko et al. |
| 4,813,280 A | 3/1989 | Miller et al. |
| 4,820,281 A | 4/1989 | Lawler |
| 4,828,545 A | 5/1989 | Epstein et al. |
| 4,832,299 A | 5/1989 | Gorton et al. |
| 4,840,345 A | 6/1989 | Neil et al. |
| 4,842,584 A | 6/1989 | Pastrone et al. |
| 4,844,397 A | 7/1989 | Skakoon et al. |
| 4,845,487 A | 7/1989 | Frantz et al. |
| 4,846,636 A | 7/1989 | Danby et al. |
| 4,856,339 A | 8/1989 | Williams |
| 4,857,048 A | 8/1989 | Simons et al. |
| 4,857,050 A | 8/1989 | Lentz et al. |
| 4,858,548 A | 8/1989 | Echeverria |
| 4,865,584 A | 9/1989 | Epstein et al. |
| 4,881,413 A | 11/1989 | Georgi et al. |
| D305,060 S | 12/1989 | Bisha'et al. |
| 4,892,656 A | 1/1990 | Pietzsch |
| 4,898,578 A | 2/1990 | Rubalcaba, Jr. |
| 4,925,444 A | 5/1990 | Orkin et al. |
| 4,927,411 A | 5/1990 | Pastrone et al. |
| 4,935,014 A | 6/1990 | Haber |
| 4,938,079 A | 7/1990 | Goldberg |
| 4,947,856 A | 8/1990 | Beard |
| 5,014,798 A | 5/1991 | Glynn |
| 5,017,192 A | 5/1991 | Dodge et al. |
| 5,031,465 A | 7/1991 | Redus |
| 5,034,004 A | 7/1991 | Crankshaw |
| 5,062,775 A | 11/1991 | Orth |
| 5,085,644 A | 2/1992 | Watson et al. |
| 5,098,262 A | 3/1992 | Wecker et al. |
| 5,102,083 A | 4/1992 | Baskas |
| 5,102,392 A | 4/1992 | Sakai et al. |
| 5,113,904 A | 5/1992 | Aslanian |
| 5,138,743 A | 8/1992 | Hoffman |
| 5,125,891 A | 9/1992 | Hossain et al. |
| 5,152,753 A | 10/1992 | Laguette et al. |
| 5,154,513 A | 10/1992 | Beer et al. |
| 5,163,900 A | 11/1992 | Wortrich |
| 5,165,406 A | 11/1992 | Wong et al. |
| 5,165,873 A | 11/1992 | Meijer |
| 5,169,106 A | 12/1992 | Rasmussen |
| 5,177,993 A | 1/1993 | Beckman et al. |
| 5,187,746 A | 2/1993 | Narisawa |

(56) References Cited

U.S. PATENT DOCUMENTS

| | | |
|---|---|---|
| 5,192,269 A | 3/1993 | Poli et al. |
| 5,205,153 A | 4/1993 | Hlavinka et al. |
| 5,207,642 A | 5/1993 | Orkin et al. |
| 5,211,626 A | 5/1993 | Frank et al. |
| 5,217,355 A | 6/1993 | Hyman et al. |
| 5,219,099 A | 6/1993 | Spence et al. |
| 5,219,327 A | 6/1993 | Okada |
| 5,219,428 A | 6/1993 | Stern |
| 5,220,920 A | 6/1993 | Gharib |
| 5,225,063 A | 7/1993 | Gumbrecht et al. |
| 5,242,406 A | 9/1993 | Gross et al. |
| 5,256,157 A | 10/1993 | Samiotes et al. |
| 5,257,978 A | 11/1993 | Haber et al. |
| 5,270,702 A | 12/1993 | Krolak |
| 5,271,815 A | 12/1993 | Wong |
| 5,282,787 A | 2/1994 | Wortrich |
| 5,287,851 A | 2/1994 | Beran et al. |
| 5,292,306 A | 3/1994 | Wynkoop et al. |
| 5,302,093 A | 4/1994 | Owens et al. |
| 5,306,122 A | 4/1994 | Gebauer et al. |
| 5,309,604 A | 5/1994 | Poulsen et al. |
| 5,317,506 A | 5/1994 | Coutre et al. |
| D348,101 S | 6/1994 | Poli et al. |
| 5,322,253 A | 6/1994 | Stevens |
| 5,324,266 A | 6/1994 | Ambrisco et al. |
| 5,325,728 A | 7/1994 | Zimmerman et al. |
| 5,326,059 A | 7/1994 | Pryor et al. |
| 5,330,634 A | 7/1994 | Wong et al. |
| 5,332,184 A | 7/1994 | Davis |
| 5,345,932 A | 9/1994 | Yafuso et al. |
| 5,346,466 A | 9/1994 | Yerlikaya et al. |
| 5,358,205 A | 10/1994 | Starkey et al. |
| 5,364,364 A | 11/1994 | Kasvikis et al. |
| D353,667 S | 12/1994 | Tsubota et al. |
| 5,378,126 A | 1/1995 | Abrahamson et al. |
| 5,378,231 A | 1/1995 | Johnson et al. |
| 5,380,665 A | 1/1995 | Cusack et al. |
| 5,382,232 A | 1/1995 | Hague et al. |
| D355,716 S | 2/1995 | Nash et al. |
| 5,395,320 A | 3/1995 | Padda et al. |
| 5,401,256 A | 3/1995 | Stone et al. |
| 5,403,277 A | 4/1995 | Dodge et al. |
| 5,417,119 A | 5/1995 | Smoll |
| 5,417,395 A | 5/1995 | Fowler et al. |
| 5,421,209 A | 6/1995 | Redus |
| 5,421,328 A | 6/1995 | Bedingham |
| 5,431,174 A | 7/1995 | Knute |
| 5,431,509 A | 7/1995 | Anderson et al. |
| 5,431,627 A | 7/1995 | Pastrone et al. |
| 5,437,635 A | 8/1995 | Fields et al. |
| 5,445,506 A | 8/1995 | Afflerbaugh et al. |
| 5,445,621 A | 8/1995 | Poli et al. |
| 5,445,622 A | 8/1995 | Brown |
| 5,450,758 A | 9/1995 | Smoll |
| 5,453,098 A | 9/1995 | Botts et al. |
| 5,462,052 A | 10/1995 | Gehrich |
| 5,462,256 A | 10/1995 | Minick et al. |
| 5,463,906 A | 11/1995 | Spani et al. |
| 5,465,938 A | 11/1995 | Werge et al. |
| 5,482,446 A | 1/1996 | Williamson et al. |
| D367,528 S | 2/1996 | Martson et al. |
| 5,489,265 A | 2/1996 | Montalvo et al. |
| 5,489,486 A | 2/1996 | Glover |
| 5,505,828 A | 4/1996 | Wong et al. |
| 5,515,713 A | 5/1996 | Saugues et al. |
| 5,524,475 A | 6/1996 | Kolpak |
| 5,527,289 A | 6/1996 | Foster et al. |
| 5,538,807 A | 7/1996 | Hagiuda |
| 5,540,561 A | 7/1996 | Johnson et al. |
| 5,551,300 A | 9/1996 | Vurek et al. |
| 5,554,013 A | 9/1996 | Owens et al. |
| 5,554,112 A | 9/1996 | Walbrink et al. |
| D376,199 S | 12/1996 | Rozek et al. |
| 5,584,671 A | 12/1996 | Schweitzer, Jr. et al. |
| 5,586,868 A | 12/1996 | Lawless et al. |
| 5,601,420 A | 2/1997 | Warner et al. |
| 5,601,445 A | 2/1997 | Schipper et al. |
| 5,603,613 A | 2/1997 | Butterfield et al. |
| 5,609,572 A | 3/1997 | Lang |
| 5,611,784 A | 3/1997 | Barresi et al. |
| 5,616,124 A | 4/1997 | Hague et al. |
| 5,626,151 A | 5/1997 | Linden |
| 5,628,309 A | 5/1997 | Brown |
| 5,628,731 A | 5/1997 | Dodge et al. |
| 5,630,710 A | 5/1997 | Tune et al. |
| 5,647,491 A | 7/1997 | Foster et al. |
| 5,647,852 A | 7/1997 | Atkinson |
| 5,651,775 A | 7/1997 | Walker et al. |
| 5,657,000 A | 8/1997 | Ellingboe |
| 5,658,133 A | 8/1997 | Anderson et al. |
| 5,672,832 A | 9/1997 | Cucci et al. |
| 5,673,588 A | 10/1997 | Raymond |
| 5,681,019 A | 10/1997 | Boyce |
| 5,693,891 A | 12/1997 | Brown et al. |
| 5,697,899 A | 12/1997 | Hillman et al. |
| 5,697,916 A | 12/1997 | Schraga |
| 5,709,663 A | 1/1998 | Younkes |
| D390,574 S | 2/1998 | Ashcraft |
| D390,654 S | 2/1998 | Alsberg et al. |
| 5,713,509 A | 2/1998 | Correll |
| 5,713,856 A | 2/1998 | Eggers et al. |
| 5,718,569 A | 2/1998 | Holst |
| 5,723,773 A | 3/1998 | Bryan |
| 5,728,069 A | 3/1998 | Montevecchi et al. |
| 5,728,074 A | 3/1998 | Castellano et al. |
| 5,733,061 A | 3/1998 | Child |
| 5,736,650 A | 4/1998 | Hiron et al. |
| 5,738,662 A | 4/1998 | Shannon et al. |
| 5,740,810 A | 4/1998 | Johnson et al. |
| 5,745,378 A | 4/1998 | Barker et al. |
| D394,440 S | 5/1998 | Chen |
| 5,752,918 A | 5/1998 | Fowler et al. |
| 5,755,563 A | 5/1998 | Clegg et al. |
| 5,755,683 A | 5/1998 | Houle et al. |
| 5,758,643 A | 6/1998 | Wong et al. |
| 5,763,760 A | 6/1998 | Gumbrecht et al. |
| 5,772,166 A | 6/1998 | Adams |
| 5,772,637 A | 6/1998 | Heinzmann et al. |
| 5,782,611 A | 7/1998 | Neftel et al. |
| 5,782,805 A | 7/1998 | Meinzer et al. |
| 5,793,216 A | 8/1998 | Constant |
| 5,804,048 A | 9/1998 | Wong et al. |
| 5,805,455 A | 9/1998 | Lipps |
| 5,807,345 A | 9/1998 | Grabenkort |
| 5,812,419 A | 9/1998 | Chupp et al. |
| 5,814,015 A | 9/1998 | Gargano et al. |
| 5,816,779 A | 10/1998 | Lawless et al. |
| 5,848,971 A | 12/1998 | Fowler et al. |
| 5,853,386 A | 12/1998 | Davis et al. |
| 5,868,696 A | 2/1999 | Giesler et al. |
| 5,868,710 A | 2/1999 | Battiato et al. |
| 5,868,712 A | 2/1999 | Briggs et al. |
| 5,891,051 A | 4/1999 | Han et al. |
| 5,895,371 A | 4/1999 | Levitas et al. |
| 5,902,253 A | 5/1999 | Pfeiffer et al. |
| 5,904,666 A | 5/1999 | DeDecker et al. |
| 5,910,808 A | 6/1999 | Fukasawa et al. |
| 5,925,022 A | 7/1999 | Battiato et al. |
| 5,932,175 A | 8/1999 | Knute et al. |
| 5,935,099 A | 8/1999 | Peterson et al. |
| 5,938,638 A | 8/1999 | Passariello et al. |
| 5,939,326 A | 8/1999 | Chupp et al. |
| 5,941,846 A | 8/1999 | Duffy et al. |
| 5,944,660 A | 8/1999 | Kimball et al. |
| 5,947,911 A | 9/1999 | Wong et al. |
| 5,954,485 A | 9/1999 | Johnson et al. |
| 5,989,222 A | 11/1999 | Cole et al. |
| 6,004,292 A | 12/1999 | Battiato et al. |
| 6,007,941 A | 12/1999 | Hermann et al. |
| 6,017,318 A | 1/2000 | Gauthier et al. |
| 6,027,445 A | 2/2000 | Von Bahr |
| 6,027,479 A | 2/2000 | Alei et al. |
| 6,032,536 A | 3/2000 | Peeters et al. |
| D424,692 S | 5/2000 | Monaghan et al. |

(56) References Cited

U.S. PATENT DOCUMENTS

| | | |
|---|---|---|
| 6,056,522 A | 5/2000 | Johnson |
| 6,068,615 A | 5/2000 | Brown et al. |
| 6,080,583 A | 6/2000 | Von Bahr |
| 6,085,574 A | 7/2000 | Neftel et al. |
| 6,090,071 A | 7/2000 | Kriesel et al. |
| 6,099,470 A | 8/2000 | Bahr |
| 6,105,442 A | 8/2000 | Kriesel et al. |
| 6,106,498 A | 8/2000 | Friedli et al. |
| 6,109,460 A | 8/2000 | Herlevi et al. |
| 6,110,153 A | 8/2000 | Davis |
| 6,110,410 A | 8/2000 | Owens et al. |
| RE36,871 E | 9/2000 | Epstein et al. |
| 6,117,290 A | 9/2000 | Say et al. |
| 6,123,827 A | 9/2000 | Wong et al. |
| 6,165,154 A | 12/2000 | Gray et al. |
| 6,186,752 B1 | 2/2001 | Deniega et al. |
| 6,186,977 B1 | 2/2001 | Andrews et al. |
| 6,186,983 B1 | 2/2001 | Von Bahr |
| 6,203,528 B1 | 3/2001 | Deckert |
| 6,210,361 B1 | 4/2001 | Kamen et al. |
| 6,221,065 B1 | 4/2001 | Davis |
| 6,231,320 B1 | 5/2001 | Lawless et al. |
| 6,237,398 B1 | 5/2001 | Porat et al. |
| 6,250,132 B1 | 6/2001 | Drzewiecki |
| 6,254,572 B1 | 7/2001 | Knipfer et al. |
| 6,261,262 B1 | 7/2001 | Briggs |
| 6,269,704 B1 | 8/2001 | Ziv et al. |
| 6,270,455 B1 | 8/2001 | Brown |
| 6,272,934 B1 | 8/2001 | Rajan et al. |
| 6,277,099 B1 | 8/2001 | Strowe et al. |
| 6,285,155 B1 | 9/2001 | Maske et al. |
| 6,290,681 B1 | 9/2001 | Brown |
| 6,325,264 B1 | 12/2001 | Omosako |
| 6,349,740 B1 | 2/2002 | Cho et al. |
| D454,884 S | 3/2002 | Christiansen et al. |
| 6,364,857 B1 | 4/2002 | Gray et al. |
| 6,385,505 B1 | 5/2002 | Lipps |
| 6,386,050 B1 | 5/2002 | Yin et al. |
| 6,390,120 B1 | 5/2002 | Guala |
| 6,396,583 B1 | 5/2002 | Clare |
| 6,409,707 B1 | 6/2002 | Guala |
| 6,422,256 B1 | 7/2002 | Balazy et al. |
| 6,445,053 B1 | 9/2002 | Cho |
| 6,463,394 B1 | 10/2002 | Von Bahr |
| 6,464,667 B1 | 10/2002 | Kamen et al. |
| 6,478,065 B1 | 11/2002 | Haberstroh et al. |
| 6,482,185 B1 | 11/2002 | Hartmann |
| 6,488,652 B1 | 12/2002 | Weijand et al. |
| 6,489,896 B1 | 12/2002 | Platt |
| 6,494,694 B2 | 12/2002 | Lawless et al. |
| 6,503,221 B1 | 1/2003 | Briggs |
| 6,515,487 B1 | 2/2003 | Dawson |
| 6,519,569 B1 | 2/2003 | White et al. |
| 6,537,258 B1 | 3/2003 | Guala |
| 6,558,125 B1 | 5/2003 | Futterknecht |
| 6,565,054 B2 | 5/2003 | Weesner et al. |
| 6,568,416 B2 | 5/2003 | Tucker et al. |
| D475,721 S | 6/2003 | Harper et al. |
| 6,578,435 B2 | 6/2003 | Gould et al. |
| RE38,189 E | 7/2003 | Walker et al. |
| 6,595,943 B1 | 7/2003 | Burbank |
| 6,599,746 B1 | 7/2003 | Gumbrecht |
| 6,609,047 B1 | 8/2003 | Lipps |
| D479,248 S | 9/2003 | Gist et al. |
| 6,623,470 B2 | 9/2003 | Munis et al. |
| D481,121 S | 10/2003 | Evans |
| 6,635,033 B1 | 10/2003 | Hill et al. |
| 6,645,142 B2 | 11/2003 | Braig et al. |
| 6,656,148 B2 | 12/2003 | Das et al. |
| D485,356 S | 1/2004 | Evans |
| 6,672,561 B2 | 1/2004 | Kerg et al. |
| 6,685,668 B1 | 2/2004 | Cho et al. |
| 6,685,670 B2 | 2/2004 | Miles et al. |
| 6,685,678 B2 | 2/2004 | Evans et al. |
| 6,695,803 B1 | 2/2004 | Robinson et al. |
| 6,700,174 B1 | 3/2004 | Mui et al. |
| 6,700,784 B2 | 3/2004 | Huang et al. |
| 6,709,417 B1 | 3/2004 | Houle et al. |
| 6,722,211 B1 | 4/2004 | Ciobanu et al. |
| 6,726,656 B2 | 4/2004 | Kamen et al. |
| 6,726,657 B1 | 4/2004 | Dedig et al. |
| 6,736,801 B1 | 5/2004 | Gallagher |
| 6,749,403 B2 | 6/2004 | Bryant et al. |
| 6,755,086 B2 | 6/2004 | Salamitou |
| 6,755,391 B2 | 6/2004 | Newton et al. |
| 6,760,643 B2 | 7/2004 | Lipps |
| 6,813,964 B1 | 11/2004 | Clark et al. |
| D500,326 S | 12/2004 | Fathallah et al. |
| 6,827,709 B2 | 12/2004 | Fujii |
| 6,872,297 B2 | 3/2005 | Mansouri et al. |
| D504,507 S | 4/2005 | Ziegler et al. |
| 6,890,315 B1 | 5/2005 | Levin et al. |
| 6,905,314 B2 | 6/2005 | Danby |
| 6,915,679 B2 | 7/2005 | Chien et al. |
| 6,920,795 B2 | 7/2005 | Bischoff et al. |
| 6,929,619 B2 | 8/2005 | Fago et al. |
| 6,932,796 B2 | 8/2005 | Sage et al. |
| 6,935,189 B2 | 8/2005 | Richards |
| 6,935,192 B2 | 8/2005 | Sobek et al. |
| 6,939,111 B2 | 9/2005 | Huitt et al. |
| 6,942,473 B2 | 9/2005 | Abrahamson et al. |
| 6,942,636 B2 | 9/2005 | Holst et al. |
| 6,964,204 B2 | 11/2005 | Clark et al. |
| 6,969,419 B1 | 11/2005 | Macemon |
| 6,975,922 B2 | 12/2005 | Duncan et al. |
| 6,981,960 B2 | 1/2006 | Cho et al. |
| D515,205 S | 2/2006 | Fathalla et al. |
| 7,004,727 B2 | 2/2006 | Kline et al. |
| 7,008,393 B2 | 3/2006 | Robinson et al. |
| RE39,075 E | 4/2006 | Verkaart |
| 7,029,105 B2 | 4/2006 | Matsuba et al. |
| 7,037,428 B1 | 5/2006 | Robinson et al. |
| 7,041,076 B1 | 5/2006 | Westberg et al. |
| 7,044,002 B2 | 5/2006 | Ericson et al. |
| 7,059,184 B2 | 6/2006 | Kanouda et al. |
| 7,061,766 B2 | 6/2006 | Wainwright et al. |
| 7,070,578 B2 | 7/2006 | Leukanech et al. |
| 7,074,209 B2 | 7/2006 | Evans et al. |
| 7,077,650 B2 | 7/2006 | Johnstone |
| 7,082,843 B2 | 8/2006 | Clark et al. |
| 7,087,036 B2 | 8/2006 | Busby et al. |
| 7,096,729 B2 | 8/2006 | Repko et al. |
| 7,115,113 B2 | 10/2006 | Evans et al. |
| 7,140,070 B2 | 11/2006 | Yuta et al. |
| 7,152,469 B2 | 12/2006 | Milleker et al. |
| 7,160,087 B2 | 1/2007 | Fathallah et al. |
| 7,161,488 B2 | 1/2007 | Frasch |
| 7,162,290 B1 | 1/2007 | Levin |
| 7,162,927 B1 | 1/2007 | Selvan et al. |
| 7,169,128 B2 | 1/2007 | Kriesel et al. |
| 7,190,275 B2 | 3/2007 | Goldberg et al. |
| 7,258,534 B2 | 8/2007 | Fathallah et al. |
| 7,327,273 B2 | 2/2008 | Hung et al. |
| 7,364,562 B2 | 4/2008 | Braig et al. |
| 7,367,942 B2 | 5/2008 | Grage et al. |
| 7,377,148 B2 | 5/2008 | Cassidy et al. |
| 7,415,895 B2 | 8/2008 | Kurisaki et al. |
| 7,462,161 B2 | 12/2008 | O'Mahony et al. |
| 7,503,903 B2 | 3/2009 | Carlisle et al. |
| 7,556,616 B2 | 7/2009 | Fathallah et al. |
| 7,571,024 B2 | 8/2009 | Duncan et al. |
| 7,608,042 B2 | 10/2009 | Golberger et al. |
| 7,615,007 B2 | 11/2009 | Shults et al. |
| 7,621,892 B2 | 11/2009 | Fago et al. |
| 7,693,697 B2 | 4/2010 | Westenskow et al. |
| 7,707,897 B2 | 5/2010 | Ong |
| 7,722,537 B2 | 5/2010 | Sterling et al. |
| 7,766,630 B2 | 8/2010 | Fathallah et al. |
| 7,771,389 B2 | 8/2010 | Grispo et al. |
| 7,775,126 B2 | 8/2010 | Eckhardt |
| 7,775,127 B2 | 8/2010 | Wade |
| 7,784,330 B2 | 8/2010 | Angelescu et al. |
| 7,810,401 B2 | 10/2010 | Brown et al. |
| 7,819,838 B2 | 10/2010 | Ziegler et al. |

(56) References Cited

U.S. PATENT DOCUMENTS

| | | |
|---|---|---|
| 7,846,131 B2 | 12/2010 | Hudson et al. |
| 7,850,659 B1 | 12/2010 | Trombley, III et al. |
| 7,866,201 B1 | 1/2011 | Tutu et al. |
| 7,884,735 B2 | 2/2011 | Newkirk |
| 7,895,053 B2 | 2/2011 | Holland et al. |
| 7,896,572 B2 | 3/2011 | Fathallah et al. |
| 7,905,710 B2 | 3/2011 | Wang et al. |
| 7,933,780 B2 | 4/2011 | de la Huerga |
| 7,935,077 B2 | 5/2011 | Thor et al. |
| 7,972,296 B2 | 7/2011 | Braig et al. |
| 7,975,491 B2 | 7/2011 | Smisson, III et al. |
| 7,976,508 B2 | 7/2011 | Hoag |
| 7,998,115 B2 | 8/2011 | Bedingfield et al. |
| 8,033,157 B2 | 10/2011 | Yardimci et al. |
| 8,048,022 B2 | 11/2011 | Moy et al. |
| 8,052,644 B2 | 11/2011 | Radgowski et al. |
| 8,057,437 B2 | 11/2011 | Ziegler et al. |
| 8,061,219 B2 | 11/2011 | Rezgui et al. |
| 8,065,161 B2 | 11/2011 | Howard et al. |
| 8,065,924 B2 | 11/2011 | Ziegler et al. |
| 8,105,269 B2 | 1/2012 | Zhou et al. |
| 8,147,448 B2 | 4/2012 | Sundar et al. |
| 8,149,131 B2 | 4/2012 | Blomquist |
| 8,152,486 B2 | 4/2012 | Fathallah et al. |
| 8,219,413 B2 | 7/2012 | Martinez et al. |
| 8,256,984 B2 | 9/2012 | Fathallah et al. |
| 8,258,973 B2 | 9/2012 | Newkirk |
| 8,286,977 B2 | 10/2012 | Butler et al. |
| 8,313,308 B2 | 11/2012 | Lawless et al. |
| 8,315,885 B2 | 11/2012 | Krogh et al. |
| 8,317,698 B2 | 11/2012 | Lowery |
| 8,380,536 B2 | 2/2013 | Howard et al. |
| 8,403,908 B2 | 3/2013 | Jacobson et al. |
| D679,800 S | 4/2013 | Gusky et al. |
| 8,417,311 B2 | 4/2013 | Rule |
| 8,449,500 B2 | 5/2013 | DelCastillo et al. |
| 8,449,524 B2 | 5/2013 | Braig et al. |
| 8,491,523 B2 | 7/2013 | Thor et al. |
| 8,518,021 B2 | 8/2013 | Stewart et al. |
| 8,523,797 B2 | 9/2013 | Lowery et al. |
| 8,523,813 B2 | 9/2013 | Grispo et al. |
| 8,581,454 B2 | 11/2013 | Corrington et al. |
| 8,591,491 B2 | 11/2013 | Moy et al. |
| 8,657,778 B2 | 2/2014 | Ziegler et al. |
| 8,666,769 B2 | 3/2014 | Butler et al. |
| D703,311 S | 4/2014 | Daly |
| 8,731,960 B2 | 5/2014 | Butler et al. |
| 8,768,719 B2 | 7/2014 | Wehba et al. |
| 8,777,590 B2 | 7/2014 | Moy et al. |
| 8,801,656 B2 | 8/2014 | Lowery et al. |
| 8,926,562 B2 | 1/2015 | Fathallah et al. |
| D728,779 S | 5/2015 | Sabin et al. |
| D734,475 S | 7/2015 | Ross |
| 9,072,831 B2 | 7/2015 | Kelly et al. |
| D736,370 S | 8/2015 | Sabin et al. |
| 9,174,145 B2 | 11/2015 | Weissenbach et al. |
| D752,736 S | 3/2016 | Chandrasenan et al. |
| D759,230 S | 6/2016 | Gordon et al. |
| D759,804 S | 6/2016 | Singh et al. |
| D765,832 S | 9/2016 | Hochman et al. |
| D767,756 S | 9/2016 | Sabin |
| 9,468,713 B2 | 10/2016 | Hoenninger, III |
| D776,802 S | 1/2017 | Loew et al. |
| 9,545,475 B2 | 1/2017 | Borges et al. |
| D797,275 S | 9/2017 | Evans et al. |
| 9,799,274 B2 | 10/2017 | Alberti et al. |
| D804,017 S | 11/2017 | Sabin |
| D805,183 S | 12/2017 | Sabin et al. |
| 9,849,233 B1 | 12/2017 | Edwards et al. |
| D814,021 S | 3/2018 | Sabin |
| D815,726 S | 4/2018 | Bjelovuk et al. |
| D817,479 S | 5/2018 | Sabin et al. |
| D817,480 S | 5/2018 | Sabin et al. |
| 10,034,975 B2 | 7/2018 | McLennan et al. |
| 10,039,878 B2 | 8/2018 | Gamelin |
| D830,546 S | 10/2018 | Lacy et al. |
| D831,820 S | 10/2018 | Petersen |
| D831,821 S | 10/2018 | Petersen |
| 10,143,795 B2 | 12/2018 | Chen |
| 10,260,161 B2 | 4/2019 | Rauenbusch et al. |
| D859,634 S | 9/2019 | Hochman et al. |
| D859,638 S | 9/2019 | Swanbury et al. |
| D871,572 S | 12/2019 | Lacy et al. |
| D883,472 S | 5/2020 | Hogerwerf et al. |
| D890,914 S | 7/2020 | Ghodsi et al. |
| D891,607 S | 7/2020 | Bjelovuk et al. |
| D899,584 S | 10/2020 | Carrubba et al. |
| D899,598 S | 10/2020 | Lucio |
| D903,094 S | 11/2020 | Ghodsi et al. |
| 10,918,787 B2 | 2/2021 | Shubinsky et al. |
| D916,275 S | 4/2021 | Kolenda et al. |
| D921,190 S | 6/2021 | Shor et al. |
| D939,079 S | 12/2021 | Harris et al. |
| 11,213,619 B2 | 1/2022 | McLennan et al. |
| 2001/0007932 A1 | 7/2001 | Kamen et al. |
| 2001/0009610 A1 | 7/2001 | Augustine et al. |
| 2001/0044602 A1 | 11/2001 | Angersbach et al. |
| 2002/0004015 A1 | 1/2002 | Carlisle et al. |
| 2002/0013551 A1 | 1/2002 | Zaitsu et al. |
| 2002/0096608 A1 | 7/2002 | Cedarberg |
| 2002/0099334 A1 | 7/2002 | Hanson et al. |
| 2002/0120229 A1 | 8/2002 | Miles et al. |
| 2002/0123741 A1 | 9/2002 | Rake et al. |
| 2003/0065537 A1 | 4/2003 | Evans |
| 2003/0127850 A1 | 7/2003 | Bischoff et al. |
| 2003/0138349 A1 | 7/2003 | Robinson et al. |
| 2003/0139701 A1 | 7/2003 | White et al. |
| 2003/0144574 A1 | 7/2003 | Heilman et al. |
| 2003/0175820 A1 | 9/2003 | Smith et al. |
| 2003/0202894 A1 | 10/2003 | Leukanech et al. |
| 2004/0025597 A1 | 2/2004 | Ericson |
| 2004/0074795 A1 | 4/2004 | Fischer |
| 2004/0082918 A1 | 4/2004 | Evans et al. |
| 2004/0176724 A1 | 9/2004 | Kamen et al. |
| 2004/0225409 A1 | 11/2004 | Duncan et al. |
| 2004/0232219 A1 | 11/2004 | Fowler |
| 2004/0249308 A1 | 12/2004 | Forssell |
| 2004/0251406 A1 | 12/2004 | Figueria |
| 2005/0006538 A1 | 1/2005 | Turi et al. |
| 2005/0038387 A1 | 2/2005 | Kriesel et al. |
| 2005/0055242 A1 | 3/2005 | Bello et al. |
| 2005/0059926 A1 | 3/2005 | Sage et al. |
| 2005/0074340 A1 | 4/2005 | Xu et al. |
| 2005/0095152 A1 | 5/2005 | Dale |
| 2005/0165384 A1 | 7/2005 | Gravesen et al. |
| 2005/0168941 A1 | 8/2005 | Sokol et al. |
| 2005/0171512 A1 | 8/2005 | Flaherty |
| 2005/0177110 A1 | 8/2005 | Azzolini |
| 2005/0209547 A1 | 9/2005 | Burbank et al. |
| 2005/0209563 A1 | 9/2005 | Hopping et al. |
| 2005/0260090 A1 | 11/2005 | Stark et al. |
| 2005/0268712 A1 | 12/2005 | Repko et al. |
| 2005/0274194 A1 | 12/2005 | Skinner et al. |
| 2005/0277911 A1 | 12/2005 | Stewart et al. |
| 2006/0030821 A1 | 2/2006 | Lee et al. |
| 2006/0042633 A1 | 3/2006 | Bishop et al. |
| 2006/0070669 A1 | 4/2006 | Mabry et al. |
| 2006/0079831 A1 | 4/2006 | Gilbert |
| 2006/0136095 A1 | 6/2006 | Rob et al. |
| 2006/0142692 A1 | 6/2006 | Jacobson et al. |
| 2006/0173253 A1 | 8/2006 | Ganapathy et al. |
| 2006/0181695 A1 | 8/2006 | Sage, Jr. |
| 2006/0187069 A1 | 8/2006 | Duan |
| 2006/0189858 A1 | 8/2006 | Sterling et al. |
| 2006/0189925 A1 | 8/2006 | Gable et al. |
| 2006/0189926 A1 | 8/2006 | Hall et al. |
| 2006/0194325 A1 | 8/2006 | Gable et al. |
| 2006/0195045 A1 | 8/2006 | Gable et al. |
| 2006/0195058 A1 | 8/2006 | Gable et al. |
| 2006/0200070 A1 | 9/2006 | Callicoat et al. |
| 2006/0200071 A1 | 9/2006 | Sterling et al. |
| 2006/0200094 A1 | 9/2006 | Holz |
| 2006/0229531 A1 | 10/2006 | Goldberger et al. |
| 2006/0235348 A1 | 10/2006 | Callicoat et al. |

(56) References Cited

U.S. PATENT DOCUMENTS

| | | |
|---|---|---|
| 2006/0241550 A1 | 10/2006 | Kamen et al. |
| 2006/0260416 A1 | 11/2006 | Sage et al. |
| 2006/0265246 A1 | 11/2006 | Hoag |
| 2006/0266128 A1 | 11/2006 | Clark et al. |
| 2007/0038188 A1 | 2/2007 | Bialecki et al. |
| 2007/0060872 A1 | 3/2007 | Hall et al. |
| 2007/0112297 A1 | 5/2007 | Plahey et al. |
| 2007/0129618 A1 | 6/2007 | Goldberger et al. |
| 2007/0151366 A1 | 7/2007 | McDonald et al. |
| 2007/0179436 A1 | 8/2007 | Braig et al. |
| 2007/0179437 A1 | 8/2007 | Grage et al. |
| 2007/0225675 A1 | 9/2007 | Robinson et al. |
| 2007/0239096 A1 | 10/2007 | Keenan et al. |
| 2007/0250339 A1 | 10/2007 | Mallett et al. |
| 2008/0039824 A1 | 2/2008 | Fathallah et al. |
| 2008/0051732 A1 | 2/2008 | Chen |
| 2008/0065420 A1 | 3/2008 | Tirinato et al. |
| 2008/0086042 A1 | 4/2008 | Brister et al. |
| 2008/0086044 A1 | 4/2008 | Brister et al. |
| 2008/0097288 A1 | 4/2008 | Levin et al. |
| 2008/0108942 A1 | 5/2008 | Brister et al. |
| 2008/0116157 A1 | 5/2008 | Fulbrook et al. |
| 2008/0145249 A1 | 6/2008 | Smisson |
| 2008/0208103 A1 | 8/2008 | Demers et al. |
| 2009/0004767 A1 | 1/2009 | Parks et al. |
| 2009/0018483 A1 | 1/2009 | Walker et al. |
| 2009/0046402 A1 | 2/2009 | Malkus et al. |
| 2009/0069743 A1 | 3/2009 | Krishnamoorthy et al. |
| 2009/0105646 A1 | 4/2009 | Hendrixson et al. |
| 2009/0143711 A1 | 6/2009 | Braig et al. |
| 2009/0240123 A1 | 9/2009 | Siebrecht et al. |
| 2010/0137778 A1 | 6/2010 | Kunjan et al. |
| 2010/0152681 A1 | 6/2010 | Mathias |
| 2010/0280486 A1 | 11/2010 | Khair et al. |
| 2011/0005606 A1 | 1/2011 | Bartels et al. |
| 2011/0015610 A1 | 1/2011 | Plahey et al. |
| 2011/0060199 A1 | 3/2011 | Robinson et al. |
| 2011/0060758 A1 | 3/2011 | Schlotterbeck et al. |
| 2011/0106462 A1 | 5/2011 | Kilburn et al. |
| 2011/0213395 A1 | 9/2011 | Corrington et al. |
| 2011/0264043 A1 | 10/2011 | Kotnick et al. |
| 2011/0264044 A1 | 10/2011 | Bartz et al. |
| 2011/0313318 A1 | 12/2011 | Rule et al. |
| 2011/0313358 A1 | 12/2011 | Hariharesan et al. |
| 2012/0035418 A1 | 2/2012 | Talbert et al. |
| 2012/0065482 A1 | 3/2012 | Robinson et al. |
| 2012/0078218 A1 | 3/2012 | Barnes |
| 2012/0130341 A1 | 5/2012 | Whitley |
| 2012/0145616 A1 | 6/2012 | Weissenbach et al. |
| 2012/0245554 A1 | 9/2012 | Kawamura |
| 2012/0271226 A1 | 10/2012 | Farrell et al. |
| 2013/0079710 A1 | 3/2013 | Krogh et al. |
| 2013/0165900 A1 | 6/2013 | Braig et al. |
| 2013/0177455 A1 | 7/2013 | Kamen et al. |
| 2013/0274669 A1 | 10/2013 | Stempfle et al. |
| 2013/0281965 A1 | 10/2013 | Kamen et al. |
| 2013/0297330 A1 | 11/2013 | Kamen et al. |
| 2015/0005935 A1 | 1/2015 | Bae et al. |
| 2015/0133861 A1 | 5/2015 | McLennan et al. |
| 2015/0167651 A1 | 6/2015 | Balteanu et al. |
| 2016/0045659 A1 | 2/2016 | Chen |
| 2017/0340809 A1 | 11/2017 | McLennan et al. |
| 2019/0059859 A1 | 2/2019 | Pinch |
| 2019/0060539 A1 | 2/2019 | Siess et al. |
| 2019/0192763 A1 | 6/2019 | McLennan et al. |
| 2022/0362457 A1 | 11/2022 | McLennan et al. |

FOREIGN PATENT DOCUMENTS

| | | |
|---|---|---|
| CN | 306797374 S | 8/2021 |
| DE | 37 42 268 | 6/1989 |
| EP | 0 197 705 | 10/1986 |
| EP | 0 306 130 | 3/1989 |
| EP | 0 396 003 | 11/1990 |
| EP | 0 423 978 | 4/1991 |
| EP | 0 429 866 | 6/1991 |
| EP | 0 447 985 | 9/1991 |
| EP | 0 450 736 | 10/1991 |
| EP | 0 483 794 | 5/1992 |
| EP | 0 510 881 | 10/1992 |
| EP | 0 569 030 | 11/1993 |
| EP | 0 477 551 | 1/1995 |
| EP | 0 481 656 | 8/1995 |
| EP | 0 697 898 | 2/1996 |
| EP | 0 839 062 | 5/1998 |
| EP | 0 891 784 | 1/1999 |
| EP | 0 960 627 | 12/1999 |
| EP | 1 177 802 | 2/2002 |
| EP | 2 742 961 | 6/2014 |
| JP | 01-265973 | 10/1989 |
| JP | 02-093917 | 7/1990 |
| JP | 09-327512 | 12/1997 |
| JP | 10-239193 | 9/1998 |
| JP | 2002-119587 | 4/2002 |
| JP | 3102285 | 3/2004 |
| JP | 2007-071695 | 3/2007 |
| JP | 2008-539964 | 11/2008 |
| JP | 4322661 | 6/2009 |
| JP | 2012-010718 | 1/2012 |
| JP | D1467576 | 4/2013 |
| JP | 2014-104011 | 6/2014 |
| JP | D1711790 | 4/2022 |
| TW | D192262 | 8/2018 |
| TW | D209965 | 2/2021 |
| WO | WO 91/016087 | 10/1991 |
| WO | WO 92/017226 | 10/1992 |
| WO | WO 93/005829 | 4/1993 |
| WO | WO 93/012828 | 7/1993 |
| WO | WO 94/009847 | 5/1994 |
| WO | WO 95/024229 | 9/1995 |
| WO | WO 95/031233 | 11/1995 |
| WO | WO 96/035472 | 11/1996 |
| WO | WO 98/013080 | 4/1998 |
| WO | WO 99/010028 | 3/1999 |
| WO | WO 99/010830 | 3/1999 |
| WO | WO 00/057941 | 10/2000 |
| WO | WO 00/066203 | 11/2000 |
| WO | WO 01/033710 | 5/2001 |
| WO | WO 01/039816 | 6/2001 |
| WO | WO 02/027276 | 4/2002 |
| WO | WO 02/036044 | 5/2002 |
| WO | WO 02/103209 | 6/2002 |
| WO | WO 02/087664 | 11/2002 |
| WO | WO 2004/069095 | 8/2004 |
| WO | WO 2004/070994 | 8/2004 |
| WO | WO 2005/000378 | 1/2005 |
| WO | WO 2005/050526 | 6/2005 |
| WO | WO 2005/082450 | 9/2005 |
| WO | WO 2005/118015 | 12/2005 |
| WO | WO 2007/008692 | 1/2007 |
| WO | WO 2007/124070 | 11/2007 |
| WO | WO 2008/057729 | 5/2008 |
| WO | WO 2008/144575 | 11/2008 |
| WO | WO 2009/021705 | 2/2009 |
| WO | WO 2009/039203 | 3/2009 |
| WO | WO 2009/039214 | 3/2009 |
| WO | WO 2010/048644 | 4/2010 |
| WO | WO 2011/159956 | 12/2011 |
| WO | WO 2014/131729 | 9/2014 |
| WO | WO 2017/144366 | 8/2017 |
| WO | WO 2020/214717 | 10/2020 |

OTHER PUBLICATIONS

"Differential Pressure Transmitter, Series PD-39 X", SensorsOne Ltd., Advertisement, Dec. 2005, pp. 2.

Galt et al., "Personal Digital Assistant-Based Drug Information Sources: Potential to Improve Medication Safety", Journal of Medical Library Association, Apr. 2005, vol. 93, No. 2, pp. 229-236.

Kutschka et al., "A New Minimized Perfusion Circuit Provides Highly Effective Ultrasound Controlled Deairing", Artificial Organs, 2007, vol. 31, No. 3, pp. 215-220.

(56) References Cited

OTHER PUBLICATIONS

Merry et al., "A New, Safety-Oriented, Integrated Drug Administration and Automated Anesthesia Record System", Anesthesia & Analgesia, Aug. 2001, vol. 93, No. 2 pp. 385-390.
Palanchon et al., "Acoustical Bubble Trapper Applied to Hemodialysis", Ultrasound in Medicine & Biology, Apr. 2008, vol. 34, No. 4, pp. 681-684.
Parlex, "Medical Device Product Examples", Johnson Medtech, Published at least as early as May of 2008, pp. 2.
Stegmayr et al., "Development of Air Micro Bubbles in the Venous Outlet Line: An In Vitro Analysis of Various Air Traps Used for Hemodialysis", Artificial Organs, 2007, vol. 31, No. 6, pp. 483-488.
International Search Report and Written Opinion received in PCT Application No. PCT/IB2016/052830, dated Aug. 9, 2016 in 9 pages.
International Preliminary Report on Patentability and Written Opinion received in PCT Application No. PCT/IB2016/052830, dated Dec. 7, 2017 in 8 pages.

(Con't)

DISPOSABLE INFUSION FLUID DELIVERY DEVICE FOR PROGRAMMABLE LARGE VOLUME DRUG DELIVERY

INCORPORATION BY REFERENCE TO ANY PRIORITY APPLICATIONS

This application is a divisional of U.S. patent application Ser. No. 15/164,277, filed on May 25, 2016, which claims the benefit of U.S. Provisional Application Ser. No. 62/166,422, filed on May 26, 2015, each of which are hereby incorporated by reference in their entirety.

FIELD OF THE DISCLOSURE

This disclosure relates to a disposable electronically controlled infusion pump system which includes a micropump and is configured for large volume drug delivery. This system is designed to be used only once for a particular patient, and then disposed of. The disposable electronically controlled infusion pump system is configured to be wirelessly controlled by a non-disposable microcontroller which has a micropump in electronic communication with an interface. The non-disposable microcontroller and the interface are configured to be reused to control additional disposable electronically controlled pump infusion systems after they are disconnected or decoupled from the first disposable electronically controlled infusion pump system. The disclosure further relates to a method for delivering infusion fluid to a patient utilizing the disposable electronically controlled infusion pump system, the non-disposable microcontroller, and the interface.

BACKGROUND

Existing infusion systems typically utilize bulky and complex electromechanical pump devices, which range from five pounds in weight up to 18 lbs., for large volume drug delivery. These electromechanical pump devices are large in size, heavy, require special mounting and handling hardware, are noisy, and are difficult to sterilize. Utilization of these electromechanical pump devices requires a substantial capital investment in procurement and periodic maintenance. Moreover, these electromechanical pump devices require the availability of adequate electric power and batteries. Other existing infusion systems may experience additional issues.

An infusion system and method is needed to reduce or eliminate one or more issues of one or more of the existing infusion systems.

SUMMARY

In one embodiment, a disposable electronically controlled infusion pump system includes at least one disposable infusion container and a disposable electronically controlled medication pumping system. The at least one disposable infusion container is configured to contain infusion fluid. The disposable electronically controlled medication pumping system is fluidly connected to the at least one disposable infusion container. The disposable electronically controlled medication pumping system includes an infusion channel, a disposable electronically controlled micropump, air in line sensors, and active valves for pumping, and may further include a microprocessor, a memory, a battery or power receiver configured to wirelessly receive power, a wireless communication device, and other components. The memory is in electronic communication with the microprocessor. The wireless communication device is configured to receive a wireless signal which wirelessly controls the disposable electronically controlled medication pumping system. The disposable electronically controlled micropump is configured to pump the infusion fluid through the infusion channel. The valves are operably connected to the infusion channel to sequence and control the flow.

In another embodiment, an infusion pump system includes a non-disposable microcontroller, at least one disposable infusion container, and at least one disposable electronically controlled medication pumping system. The non-disposable microcontroller includes a first microprocessor, a first memory in electronic communication with the first microprocessor, a battery or power source, a power transmitter connected to the battery or power source and configured to transmit power, and a first wireless communication device. The at least one disposable infusion container is configured to contain infusion fluid. The at least one disposable electronically controlled medication pumping system, controlled by the non-disposable microcontroller, is fluidly connected to the at least one disposable infusion container. The at least one disposable electronically controlled medication pumping system includes a second microprocessor, a second memory in electronic communication with the second microprocessor, a power receiver configured to wirelessly receive power from the power transmitter, a second wireless communication device configured to wirelessly communicate with the first wireless communication device, an infusion channel, a disposable electronically controlled micropump configured to pump the infusion fluid through the infusion channel, air in line sensor and valves operably connected to the infusion channel to control or sequence the flow.

In another embodiment, an infusion pump system includes a non-disposable microcontroller, at least one disposable infusion container, and at least one disposable electronically controlled medication pumping system. The non-disposable microcontroller includes a first microprocessor, a first memory in electronic communication with the first microprocessor, a battery or other power source, a power transmitter connected to the power source and configured to transmit power, and a first wireless communication device. The at least one disposable infusion container is configured to contain infusion fluid. The at least one disposable electronically controlled medication pumping system, controlled by the non-disposable microcontroller, is a ganged system fluidly connected to the at least one disposable infusion container. The at least one disposable electronically controlled medication pumping system includes an infusion channel, at least two disposable electronically controlled micropumps configured to pump the infusion fluid through the infusion channel, and valves operably connected to the infusion channel. The at least one medication pumping system may also include a second microprocessor, a second memory in electronic communication with the second microprocessor, a power receiver configured to receive power from the power transmitter, a second wireless communication device configured to wirelessly communicate with the first wireless communication device, and other components. Other of at least one disposable electronically controlled medication pumping systems may further include a third microprocessor, a third memory in electronic communication with the third microprocessor, a power receiver configured to receive power from the power transmitter, a third wireless communication device configured to wirelessly communicate with the first wireless communication device or the second wireless communication device.

In still another embodiment, a method is disclosed for delivering infusion fluid from an electronically controlled infusion system. In one step, a disposable infusion fluid delivery device is provided including at least one disposable infusion container and a disposable electronically controlled medication pumping system. In another step, a pre-determined amount of infusion fluid is disposed into the at least one disposable infusion container. In an additional step, the disposable infusion fluid delivery device containing the infusion fluid in the at least one disposable infusion container is delivered to a location at which the patient is located. In yet another step, the disposable electronically controlled medication pumping system of the disposable infusion fluid delivery device is wirelessly controlled and wirelessly powered with a non-disposable microcontroller to infuse the infusion fluid from the disposable infusion container of the disposable infusion fluid delivery device. In another step, the disposable infusion fluid delivery device is disposed of after the infusion fluid is infused so that the disposable infusion fluid delivery device is only used one time, for a single patient, The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
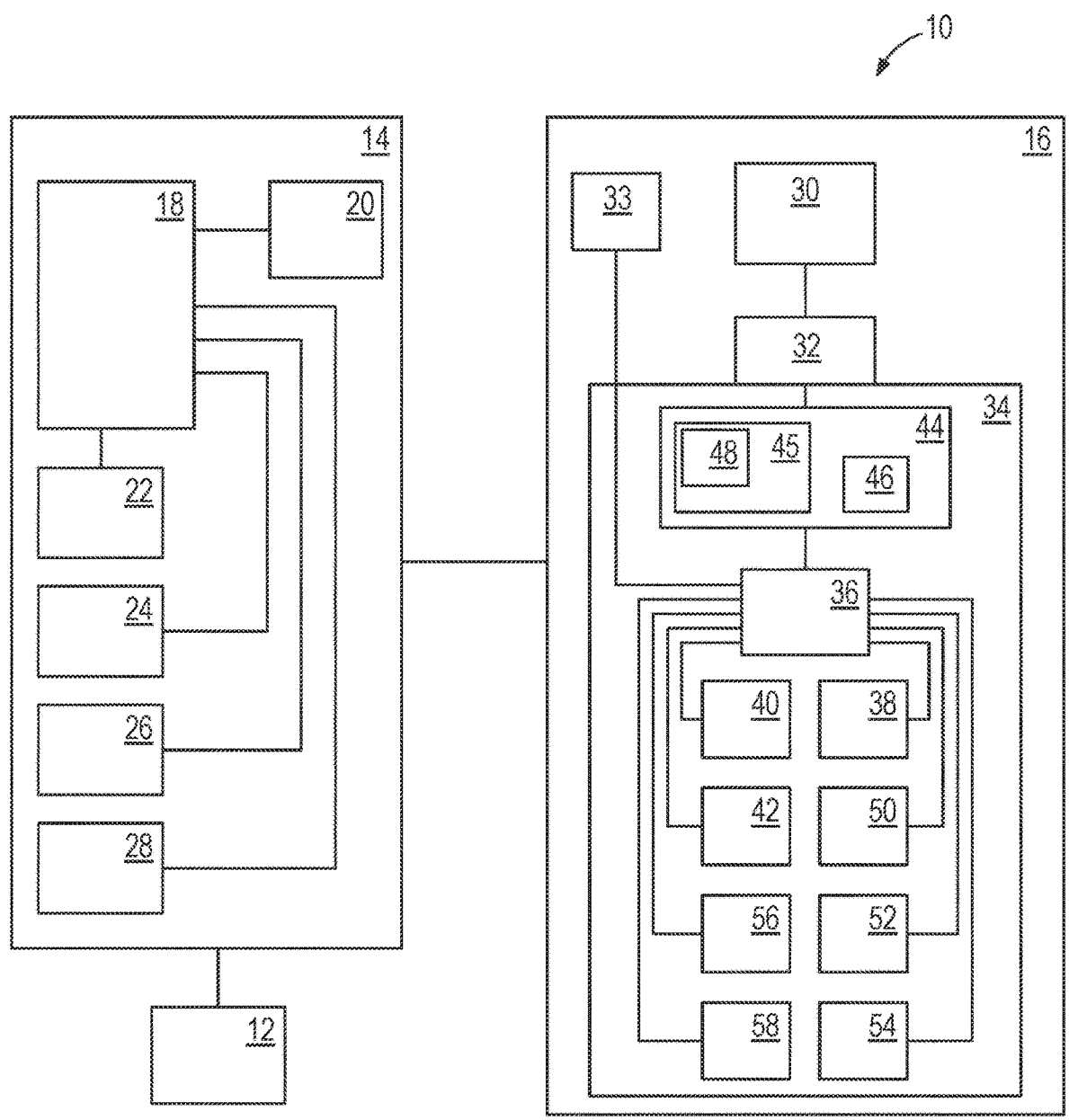
FIG. 1 illustrates a block diagram of one embodiment of an electronically controlled infusion pump system configured to infuse infusion fluid.

FIG. 1 illustrates a block diagram of one embodiment of an infusion pump system 10 configured to infuse infusion fluid. The infusion pump system 10 comprises an interface 12, a dedicated non-disposable microcontroller other devices such as existing pump systems, PC, tablets, and smartphones can be used to control disposable pumps providing they have necessary power charging attachments and wireless communication capabilities 14, and a disposable infusion fluid delivery device 16. In other embodiments, the components of the infusion pump system 10 may vary in configuration, type, or function.

For purposes of this disclosure, the term "disposable" means used once for a particular patient and then disposed of (i.e. thrown away or destroyed). For purposes of this disclosure, the term "disposable" means that the component is made of a disposable material such as plastic or another inexpensive material, which is only needed for single patient, one-time use and will not have to be sterilized after first use due to its disposal instead of re-use for the same or different (multiple) patients. For purposes of this disclosure, the term "non-disposable" means that the component will be repeatedly used for the infusion of infusion fluid to the same or varying patients. Disposable items are sometimes used in the medical field because those items come in contact with hazardous medical fluids or bodily fluids. Disposable items can be disposed of rather than being used beyond the recommended time on a given patient or on a different patient with the risk of cross-contamination, infections, or other reactions. Non-disposable items are advantageously reusable with proper isolation, cleaning, disinfection, or sterilization between uses on the same or different patients. In the case of uses on different patients, isolation, cleaning, disinfecting, or sterilizing an item between uses can help reduce the likelihood of transmission of germs, staff, bacteria or other contamination, but can be difficult to accomplish completely or effectively.

The interface 12 comprises a device which is configured to interface with the non-disposable microcontroller 14 in order to power and electronically control the non-disposable microcontroller 14 which in turn powers and electronically controls the disposable infusion fluid delivery device 16. In other embodiments, the interface 12 may be used to only power or to only electronically control the non-disposable microcontroller 14 which in turns powers and/or electronically controls the disposable infusion fluid delivery device 16. The interface 12 may comprise a smartphone, a laptop, a stand-alone computer, a nurse station, an infusion pump, or another type of device. The interface 12 may be in wired or wireless communication with the non-disposable microcontroller 14.

In one embodiment, the non-disposable microcontroller 14 and the disposable infusion fluid delivery device 16 are not configured to work at all until the non-disposable microcontroller 14 is connected to the interface 12. In another embodiment, the system 10 may be configured to operate without the interface 12 with the non-disposable microcontroller 14 exclusively powering and/or electronically controlling the disposable infusion fluid delivery device 16. The interface 12 and the non-disposable microcontroller 14 are configured to be used as many times as needed (i.e. non-disposable for repeated use) to electronically power and control differing disposable infusion fluid delivery devices 16 to deliver infusion fluid to varying patients without the interface 12 or the non-disposable microcontroller 14 ever coming into contact with either the disposable infusion fluid delivery device 16 or the infusion fluid delivered by the disposable infusion fluid delivery device 16.

The disposable infusion fluid delivery device 16, which contains a programmed pre-determined amount and type of infusion fluid for a particular patient, is configured to be a stand-alone device which is only used for the particular patient and then disposed of immediately after use. Due to the disposable infusion fluid delivery device 16 never coming into contact with either the interface 12 or the non-disposable microcontroller 14, neither the interface 12 nor the non-disposable microcontroller 14 need to be sterilized. Additionally, since the disposable infusion fluid delivery device 16 is disposed of immediately after use on the particular patient it was intended for, it also does not need to be sterilized after use. As a result, significant time and cost involved in sterilization is saved, in addition to decreasing the health risk which is typically associated with sterilization deficiencies.

The non-disposable microcontroller 14 comprises a first microprocessor 18, a first memory 20, a first wireless communication device 22, a power transmitter 24, a power source 26 such as A/C and/or a battery, and a multiplexer 28. The first processor 18 is in communication with each of the first memory 20, the first wireless communication device 22, the power transmitter 24, the battery 26, and the multiplexer 28. In other embodiments, the components of the non-disposable microcontroller 14 may vary in configuration, type, or function.

The disposable infusion fluid delivery device 16 comprises at least one disposable infusion container 30, a seal 32, a temperature sensor 33, air in line sensor, flow sensor, active valves and a disposable medication pumping system 34. In other embodiments, the components of the disposable infusion fluid delivery device 16 may vary in configuration, type, or function. The disposable medication pumping system 34 comprises a second microprocessor 36, a second memory 38, a second wireless communication device 40, a power receiver 42, an infusion channel 44, a micropump 45, valves 46, one or more piezo actuators 48, a pressure detection sensor 50, a flow detection sensor 52, an air detection sensor 54, an optional one-dimensional, two-dimensional, holographic or other type of barcode 56, and a Radio Frequency Identification Tag 58. The second processor 36 is in communication with each of the temperature sensor 33, the second memory 38, the second wireless communication device 40, the power receiver 42, the micropump 45, the active valves 46, the piezo actuators 48, the pressure detection sensor 50, the flow detection sensor 52, the air detection sensor 54, the barcode 56, and the Radio Frequency Identification Tag 58. In other embodiments, the components of the disposable medication pumping system 34 may vary in configuration, type, or function. The disposable infusion fluid delivery device 16 may comprise an integral sealed cartridge containing all components of the disposable infusion fluid delivery device 16. In other embodiments, the disposable infusion fluid delivery device 16 and its components may vary in configuration, type, or function.

In one embodiment, the non-disposable microcontroller 14 has a size in a range of 9×6 cm and a weight in a range of 100-200 grams. In another embodiment, the non-disposable microcontroller 14 has a size in a range of 6×4 cm and a weight in a range of 50-100 grams. In still another embodiment, the non-disposable microcontroller 14 has a size in a range of 5×3 cm and a weight in a range of 25-50 grams. In other embodiments, the size and weight of the non-disposable microcontroller 14 may vary.

The first microprocessor 18 operates based on programming instructions and data saved in the first memory 20. The programming instructions and data saved in the first memory 20 may be pre-stored, or obtained from any source in the hospital information system, for example through interface 12. The programming instructions and data can be obtained from the second memory 38 of the disposable infusion fluid delivery device 16, from the temperature sensor 33, from the pressure detection sensor 50, from the flow detection sensor 52, from the air detection sensor 54, from the barcode 56, from the Radio Frequency Identification Tag 58, or obtained from another source. The programming instructions and data may have been set-up in in the first memory 20 or in the second memory 38 by the drug preparer (i.e., the pharmacy) based on the patient's drug prescription from a doctor. In other embodiments, a doctor or other medical provider may set-up this information into the first memory 20 or into the second memory 38 of the disposable infusion fluid delivery device 16. In still other embodiments, the programming instructions and data may have been set-up in in the first memory 20 or in the second memory 38 in varying ways.

This data may comprise any combination of the following information: a name or identification of the drug preparer that prepared the infusion fluid contained in the disposable infusion fluid delivery device 16 (this could be a drug manufacturer, pharmacy or a compounder of the infusion fluid); a date the infusion fluid was placed into or added to the disposable infusion fluid delivery device 16; a date the infusion fluid contained in the disposable infusion fluid delivery device 16 is to expire; a manufacturing date, serial number, storage information (temperature/time) a time related to the infusion of the infusion fluid contained in the disposable infusion fluid delivery device 16; an identification of the infusion fluid contained in the disposable infusion fluid delivery device 16; a drug identification of the infusion fluid contained in the disposable infusion fluid delivery device 16, which may include a drug name and concentration, a drug identification number, and diluent information; a volume of the infusion fluid contained in the infusion delivery device 16 to be infused into the patient, or a volume of the infusion fluid infused into the patient; a flow rate (programmed and/or actual) of the infusion fluid; a duration or delivery time of the infusion fluid; a power status and/or used or remaining battery capacity of the interface 12, of the non-disposable microcontroller 14, or of the disposable infusion fluid delivery device 16; a charging status of the interface 12, of the non-disposable microcontroller 14, or of the disposable infusion fluid delivery device 16; an identification or name of the patient; a RX order number or order ID; a therapy start time; a therapy end time; a delivery time; one or more alarm conditions; a flow sensor output (flow rate); a pressure sensor output (pressure); an air-in-line sensor output (single bubble or cumulative air volume); temperature data; data regarding parameters for infusion of the infusion fluid for the particular patient; or other types of information.

The first wireless communication device 22 is configured to wirelessly communicate with the second wireless communication device 40 to allow the non-disposable microcontroller 14 and the disposable infusion fluid delivery device 16 to communicate with one another. In one embodiment, the first wireless communication device 22 and the second wireless communication device 40 may comprise a Near-Field communication device. In other embodiments, the first wireless communication device 22 and the second wireless communication device 40 may vary in type or configuration. The power transmitter 24 is configured to wirelessly transmit power or energy to the power receiver 42 (which may comprise a battery) of the disposable infusion fluid delivery device 16 in order to power the operation of disposable infusion fluid delivery device 16. In one embodiment, the power or energy transmitter 24 may utilize Near-Field Charging (capacitive, inductive energy charging) to wirelessly charge the power receiver 42. In other embodiments, the power transmitter 24 may charge the power receiver 42 utilizing varying charging methods.

The power source 26 (in non-disposable controller) is configured in one embodiment as one or more disposable or rechargeable batteries that store electrical energy and provide energy to the power transmitter 24. The multiplexer 28 is configured to electronically and wirelessly control a plurality of the disposable electronically controlled medication pumping systems 34 (only one disposable electronically controlled medication pumping system 34 is shown in FIG. 1, however FIG. 3 discussed later shows an embodiment having a plurality of the disposable electronically controlled medication pumping systems 34 being concurrently electronically and wirelessly controlled by the multiplexer 28 to deliver different infusion fluids or to provide a redundant and highly reliable infusion system). Each disposable electronically controlled medication system 34 have capability to communicate with non-disposable controller and other disposable electronically controlled medication systems. This communication capability will further increase the redundancy and reliability of the entire system and would create a topology of a complex medication delivery system that in parallel can deliver a higher combined rate of fluid delivery or in series can deliver greater accumulated volumes.

The at least one disposable infusion container 30 is configured to contain infusion fluid. At least one hermetic seal 32 permanently seals the at least one disposable infusion container 30 to the disposable medication pumping system 34 so that after the drug preparer (manufacturer or pharmacy) disposes the infusion fluid within the at least one disposable infusion container 30 no one else comes in contact with the infusion fluid other than the patient since the disposable infusion fluid delivery device 16 is disposed of after the one-time use for the intended patient. The temperature sensor 33 keeps track of a temperature the disposable infusion fluid delivery device 16 is exposed to throughout its lifetime so that it is ensured that a temperature range requirement for the infusion fluid was not violated during storage, shipping or handling prior to infusion. If the temperature range was violated during the storage or transportation of the disposable infusion container, the infusion would not be permitted. Any of the interface 12, the non-disposable microcontroller 14, and the disposable infusion fluid delivery device 16 may be configured to analyze data emulating from the temperature sensor and to compare it to pre-set temperature parameters regarding the infusion fluid in order to ensure the temperature range requirement for the infusion fluid was not violated, and if it was, to prevent infusion of the infusion fluid.

In one embodiment, the micropump disclosed in US 2011/0005606 to Bartels et al., which is hereby incorporated by reference, may be used for the disposable electronically controlled micropump 45. The disposable electronically controlled micropump 45 may contain a plurality of electrically activated piezo-actuators 48 to control the pumping of infusion fluid through the infusion channel 44. In one embodiment, the disposable electronically controlled micropump 45 is configured to pump in a range of between 0.1 to 350 milliliters of the infusion fluid per hour with accuracy of +/−10% or better. In one embodiment, the disposable electronically controlled micropump 45 has a size in a range of 8×4 cm and a weight in a range of 50-100 grams. In another embodiment, the disposable electronically controlled micropump 45 has a size in a range of 5×3 cm and a weight in a range of 30-50 grams. In still another embodiment, the disposable electronically controlled micropump 45 has a size in a range of 4×2 cm and a weight in a range of 20-40 grams. In other embodiments, the size and weight of the disposable electronically controlled micropump 45 may vary. The disposable pump can be packaged in a packaging that is capable of providing hermiticity and is compliant with FDA approved materials and capable of withstanding necessary sterilization methods including gamma irradiation, EtO, E-beam, and steam sterilization.

The second microprocessor 36 operates based on programming instructions and data saved in the second memory 38. The programming instructions and data saved in the second memory 38 may be pre-stored, or obtained from any source in the hospital information system, for example through interface 12. The programming instructions and data can be obtained from the first memory 20 of the disposable infusion fluid delivery device 16, from the temperature sensor 33, from the pressure detection sensor 50, from the flow detection sensor 52, from the air detection sensor 54, from the barcode 56, from the Radio Frequency Identification Tag 58, or obtained from another source.

This data may comprise any combination of the following information: a name or identification of the drug preparer that prepared the infusion fluid contained in the disposable infusion fluid delivery device 16; a date the infusion fluid was disposed in the disposable infusion fluid delivery device 16; a date the infusion fluid contained in the disposable infusion fluid delivery device 16 is to expire; a time related to the infusion of the infusion fluid contained in the disposable infusion fluid delivery device 16; an identification of the infusion fluid contained in the disposable infusion fluid delivery device 16; a drug identification of the infusion fluid contained in the disposable infusion fluid delivery device 16; a volume of the infusion fluid contained in the infusion delivery device 16 to be infused into the patient, or a volume of the infusion fluid infused into the patient; a flow rate of the infusion fluid; a delivery time of the infusion fluid; a power status of the interface 12, of the non-disposable microcontroller 14, or of the disposable infusion fluid delivery device 16; a charging status of the interface 12, of the non-disposable microcontroller 14, or of the disposable infusion fluid delivery device 16; an identification or name of the patient; a RX order number; a therapy start time; a therapy end time; a delivery time; one or more alarm conditions; a flow sensor output (flow rate); a pressure sensor output (pressure); an air-in-line sensor output (single bubble or cumulative air volume); temperature data; data regarding parameters for infusion of the infusion fluid for the particular patient; or other types of information. The data can be in the form of near real-time logs of the infusion delivery device's operation.

The infusion channel 44 is configured so that the infusion fluid from the at least one disposable infusion container 30 is flowed or pumped through the infusion channel 44 to the patient. The valves 46 are operatively connected to the infusion channel 44 and, along with the micropump 45, control the flow of the infusion fluid through the infusion channel 44. The valves 46 may comprise passive or active input and output valves controlled by the first microprocessor 18 or the second microprocessor 36. Use of active valves provides inherent free-flow protection and reduces the impact of backpressure and head height variability thus assuring flow rate accuracy. In other embodiments, varying types and configurations of valves 46 may be utilized.

The pressure detection sensor 50 is configured to determine a pressure of the infusion fluid flowing through the infusion channel 44 to provide real-time feedback regarding the infusion fluid pressure. In one embodiment the pressure sensor is downstream or distal with respect to the micropump 45. The flow detection sensor 52 is configured to determine a flow rate of the infusion fluid flowing through the infusion channel 44 to provide real-time feedback regarding delivery accuracy. The air detection sensor 54 is configured to determine a quantity of air in the infusion fluid flowing through the infusion channel 44 to provide real time feedback regarding the air in the infusion fluid.

The barcode 56 provides information regarding the infusion fluid, the particular patient the infusion fluid is intended for, or other information regarding the patient, the infusion fluid, and/or its delivery. The Radio Frequency Identification Tag 58 provides information such as: drug lot; program details; patient information; pump lot; pharmacy information; day and time; or other information regarding the patient, the infusion fluid, and/or its delivery.

Any of the interface 12, the non-disposable microcontroller 14, and the disposable infusion fluid delivery device 16 may be configured to analyze the information provided by the barcode 56 and/or the Radio Frequency Identification Tag 58, to analyze information stored in the first memory 20 or the second memory 38 regarding the infusion fluid, its delivery, or the particular patient, to analyze information sensed by the temperature sensor 33, the pressure detection sensor 50, the flow detection sensor 52, or the air detection sensor 54, or to analyze other information provided from other sources regarding the infusion fluid, its delivery, or the particular patient in order to ensure that patient and infusion delivery parameters are met. This may include making sure that the right infusion fluid is being infused into the right patient, making sure that the infusion fluid is infused using the correct parameters (i.e. time, flow-rate, pressure, air-prevention, temperature, amount delivered, etc.), preventing the disposable infusion fluid device 16 from being reused after it has been used on the intended patient, or ensuring that other patient and/or infusion delivery parameters are followed. If the interface 12, the non-disposable microcontroller 14, or the disposable infusion fluid delivery device 16 determine that the appropriate patient and/or infusion delivery parameters are not being followed they may be configured to adjust the infusion delivery to ensure compliance with these restraints and/or to provide an alert, alarm or stop the infusion.

Figure 2:
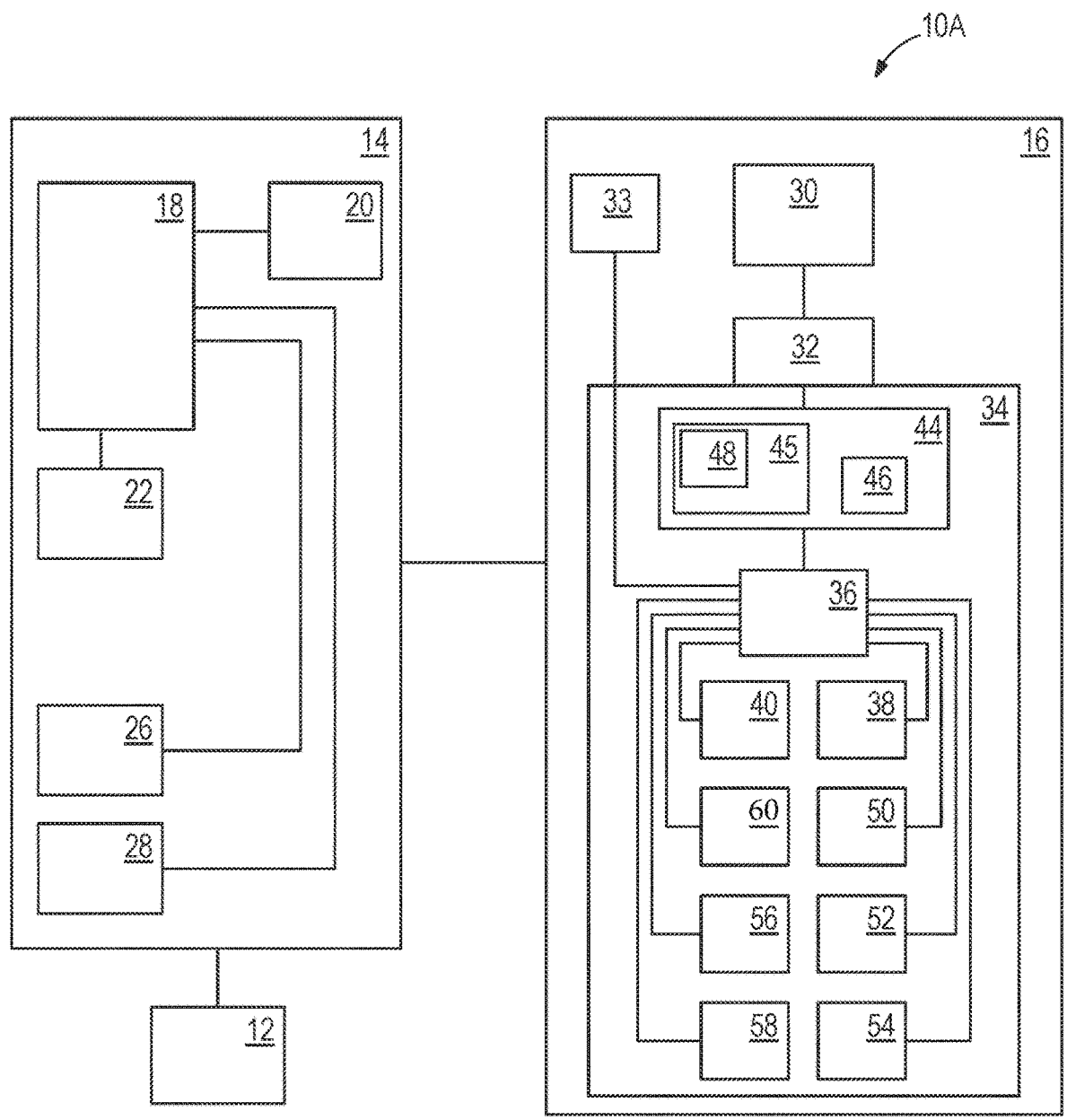
FIG. 2 illustrates a block diagram of another embodiment of an infusion pump system configured to infuse infusion fluid.

FIG. 2 illustrates a block diagram of another embodiment of an infusion pump system 10A configured to infuse medication. Components of the system 10A which are identical to the components of system 10 of FIG. 1 have been labeled with identical reference numbers as to those used in FIG. 1. The only difference structurally and functionally between the system 10A of FIG. 2 relative to the system 10 of FIG. 1 is that the power transmitter 24 and power receiver 42 have been removed in the embodiment of FIG. 2, and a battery 60 has been added to the disposable medication pumping system 34 of FIG. 2. In the embodiment of FIG. 2, rather than transmitting power wirelessly from a power transmitter 24 of the non-disposable microcontroller 14 to the power receiver 42 of the disposable electronically controlled medication pumping system 34 to power the disposable electronically controlled medication pumping system 34 as done in FIG. 1, the battery 60 of the disposable electronically controlled medication pumping system 34 is utilized to provide power to the disposable medication pumping system 34. In other embodiments, varying components may be utilized to power the disposable electronically controlled medication pumping system 34.

Figure 3:
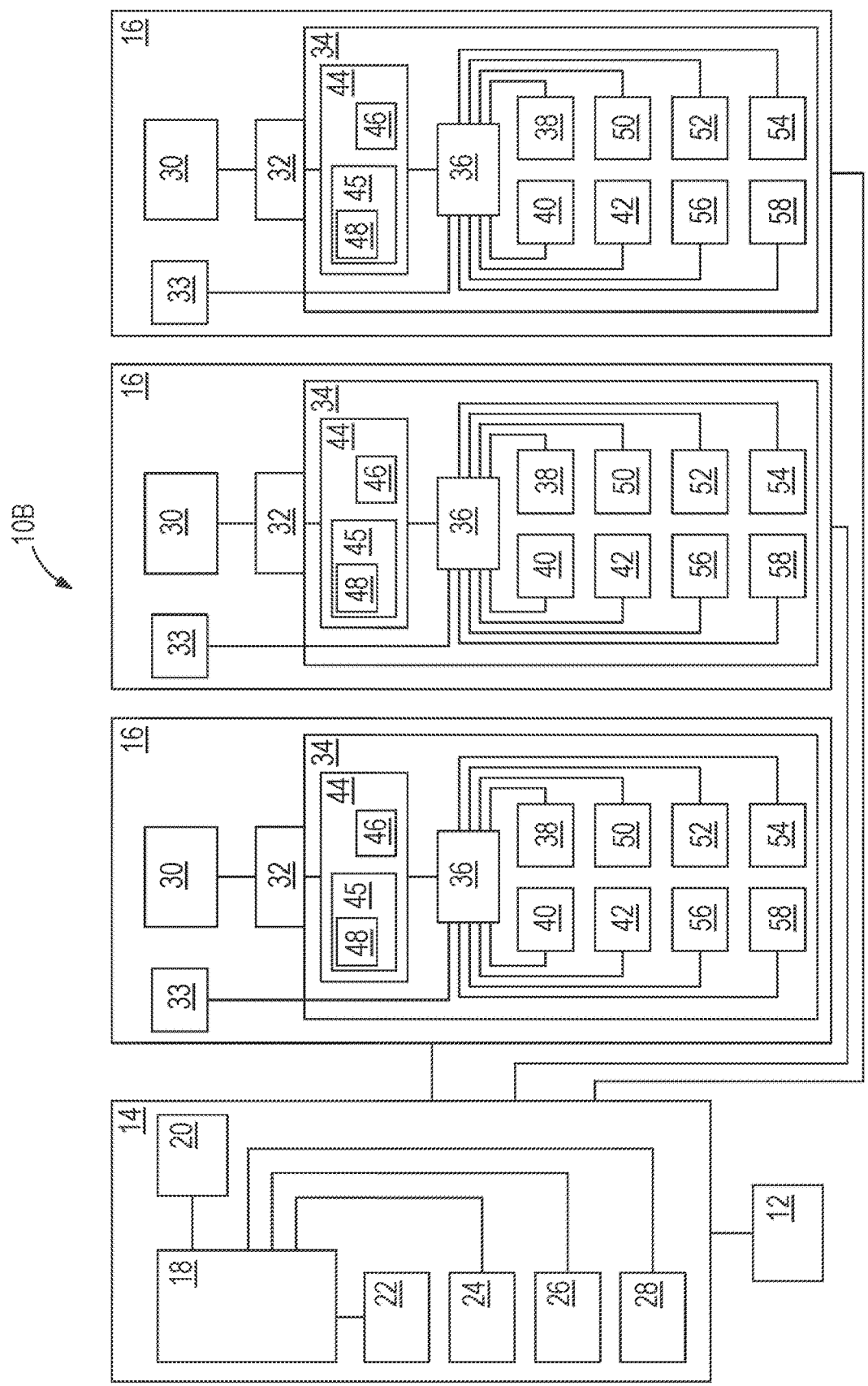
FIG. 3 illustrates a block diagram of another embodiment of an infusion pump system configured to infuse infusion fluid.

FIG. 3 illustrates a block diagram of another embodiment of an infusion pump system 10B configured to infuse infusion fluid. Components of the system 10B which are identical to the components of system 10 of FIG. 1 have been labeled with identical reference numbers as to those used in FIG. 1. The only difference structurally and functionally between the system 10B of FIG. 3 relative to the system 10 of FIG. 1 is that the system 10B of FIG. 3 comprises a plurality of the disposable infusion fluid delivery devices 16, each having at least one disposable infusion container 30 and a disposable electronically controlled medication pumping system 34, rather than having only one disposable infusion fluid delivery device 16 as in FIG. 1. The multiplexer 28 of the non-disposable microcontroller 14 is configured to concurrently electronically wirelessly control the plurality of electronically controlled medication pumping systems 34 of the plurality of disposable infusion fluid delivery devices 16 to deliver different infusion fluids or to have a redundant system. In other embodiments, varying components may be utilized to concurrently control the plurality of electronically controlled medication pumping systems 34 of one or more disposable infusion fluid delivery devices 16.

Figure 4:
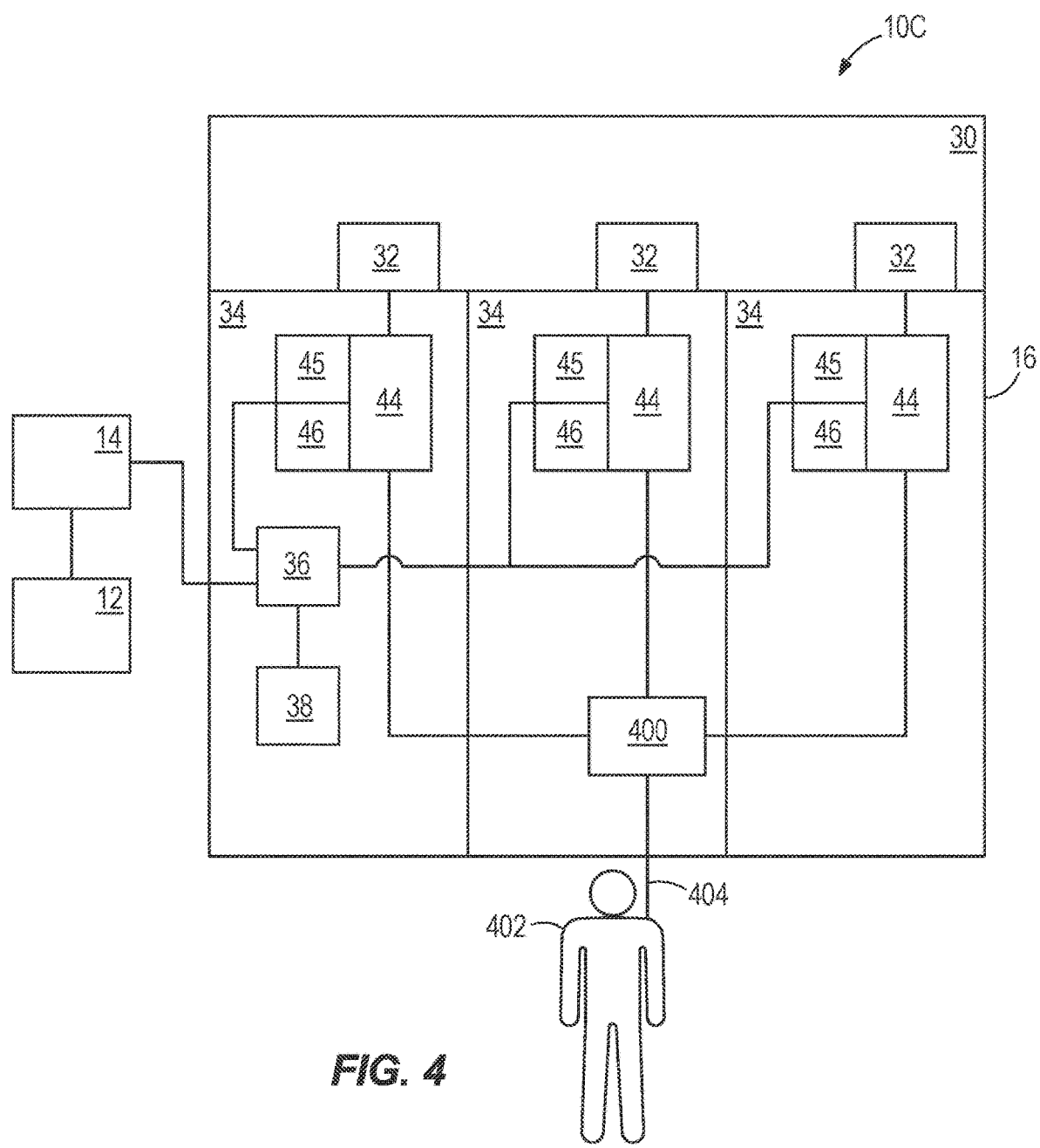
FIG. 4 illustrates a block diagram of another embodiment of an infusion pump system configured to infuse infusion fluid.

For example, in the embodiment shown in FIG. 4 where the detailed components previously shown in FIGS. 1-3 can still be present but have been omitted from the figure merely for the sake of simplicity, the infusion pump system 10C includes a plurality of electronically controlled medication pumping systems 34 that are fluidly connected to a single container 30 by respective seals 32 to form a disposable infusion fluid delivery device 16. Thus, the plurality of electronically controlled medication pumping systems 34 are each configured with an infusion channel 44, one or more valves 46 operatively associated with the infusion channel 44, and a micropump 45 to draw fluid sequentially or concurrently from a common source such as the disposable infusion container 30. The electronically controlled medication pumping systems 34 can be operated in series or in parallel to provide a desired cumulative flow rate in the range of about 0.1-2000 mL/hr. In the example shown in FIG. 4, a cumulative flow rate in the range of about 0.1-1000 mL/hr can be provided with three medication pumping systems 34 fluidly connected in parallel to a single container 30. A single second microprocessor 36 and second memory 38 can control and serve all of the plurality of medication pumping systems 34 from a location in one of the systems 34, or individual second microprocessors 36 and second memories 38 can control and serve individual electronically controlled medication pumping systems 34 respectively, or second microprocessors 36 and memories 38 can be distributed throughout the medication pumping systems in various other ways. The infusion channels 44 can be joined together with a connector 400 downstream of the micropumps 45 and upstream of the patient 402 to whom the fluid is delivered through a common output line 404. The connector 400 can be inside the disposable infusion fluid delivery device 16, as shown, or outside and downstream of it. Advantageously, the integrated disposable infusion delivery device 16 is a hermetically sealed system capable of withstanding necessary sterilization methods used on the medical fluid container 30, including gamma irradiation, EtO, E-beam, and steam sterilization.

Figure 5:
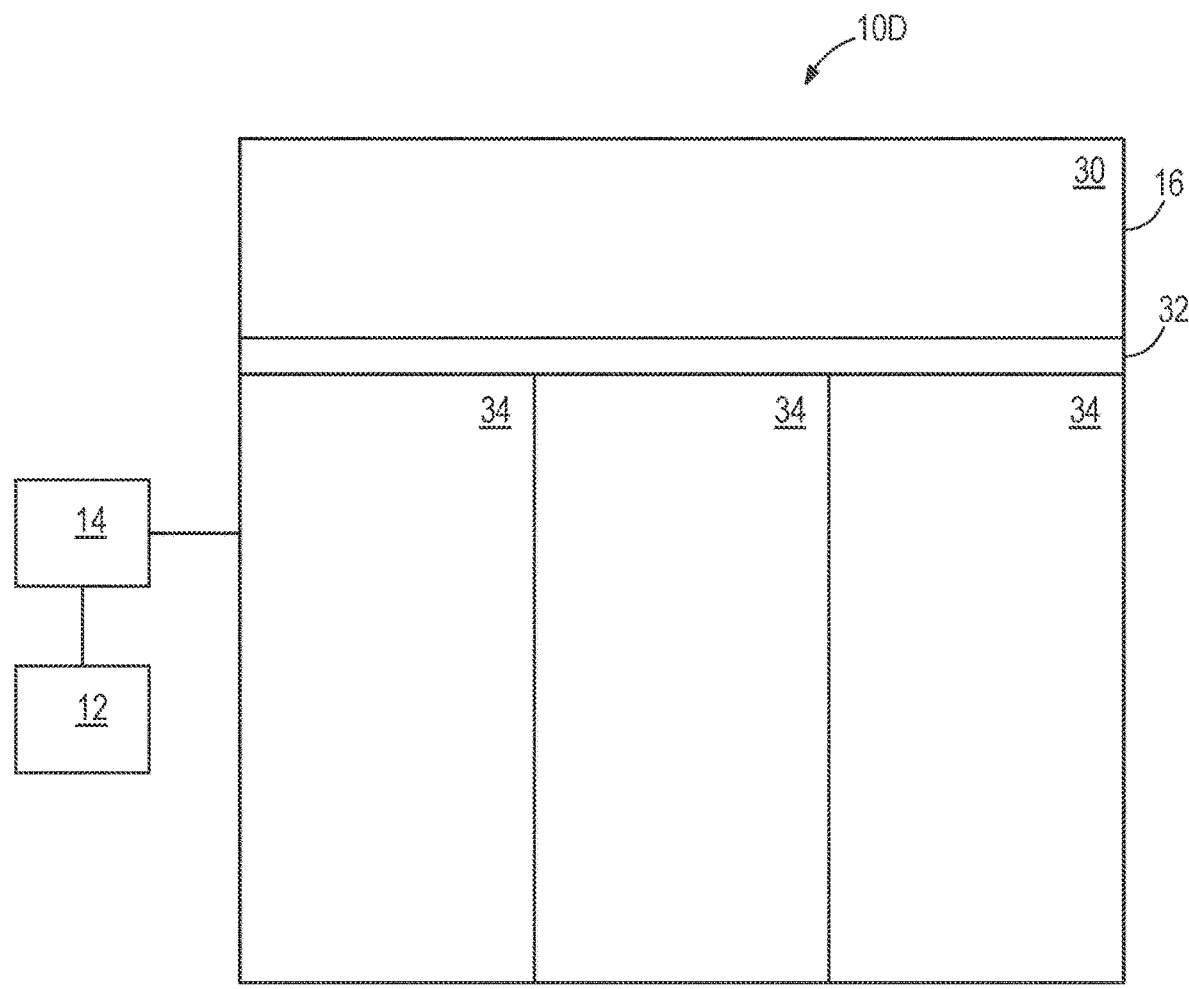
FIG. 5 illustrates a block diagram of another embodiment of an infusion pump system configured to infuse infusion fluid.

FIG. 5 illustrates another embodiment similar to those described above with respect to FIGS. 1-4 except that the infusion pump system 10D has a single seal 32 or gasket, which is used to integrally attach and fluidly connect the plurality of electronically controlled medication pumping systems 34 to the container 30 or flexible intravenous solution bag to form an integrated disposable infusion fluid delivery device 16.

Figure 6:
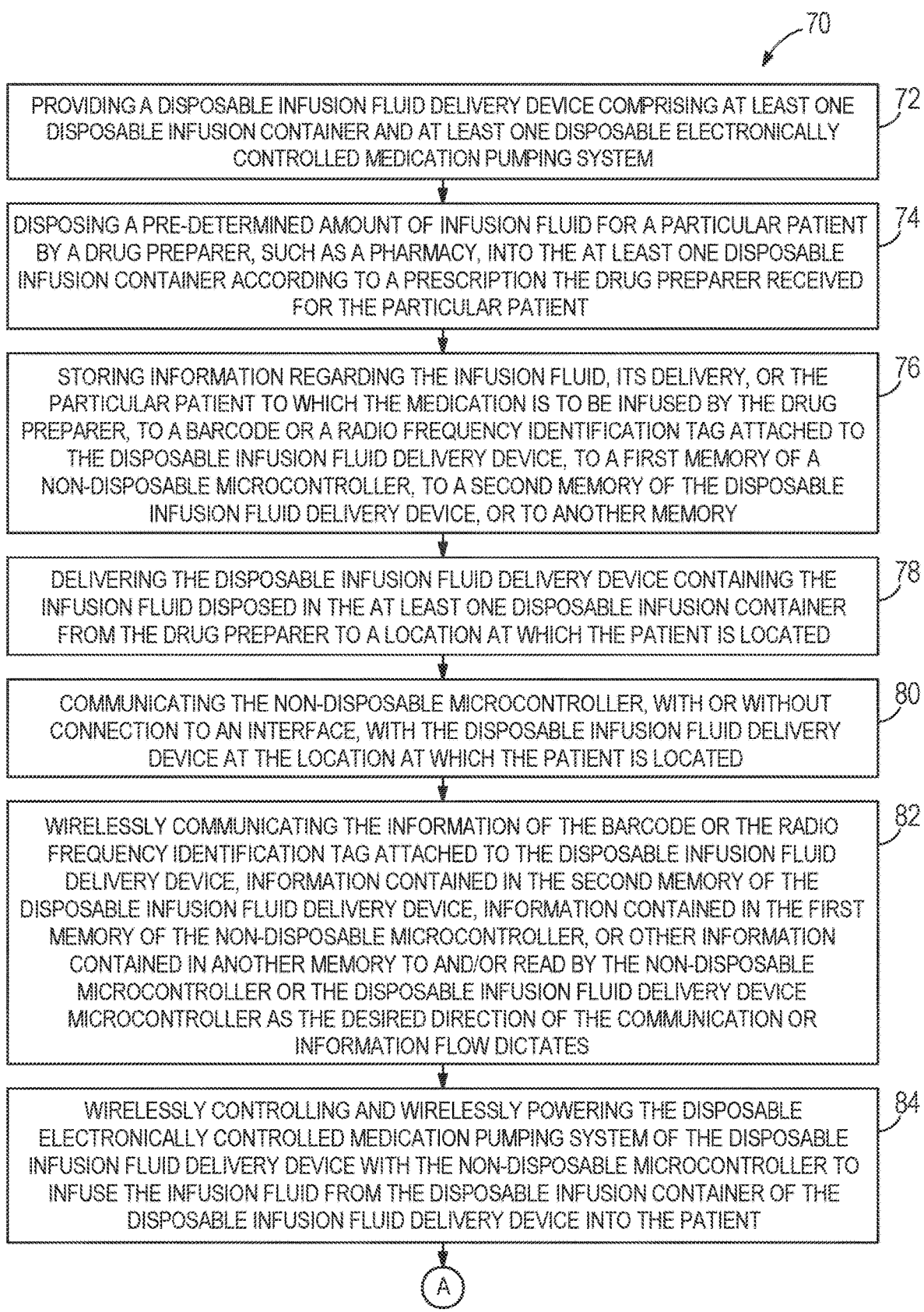
FIG. 6 illustrates a flowchart of one embodiment of a method for delivering infusion fluid.
Figure 6:
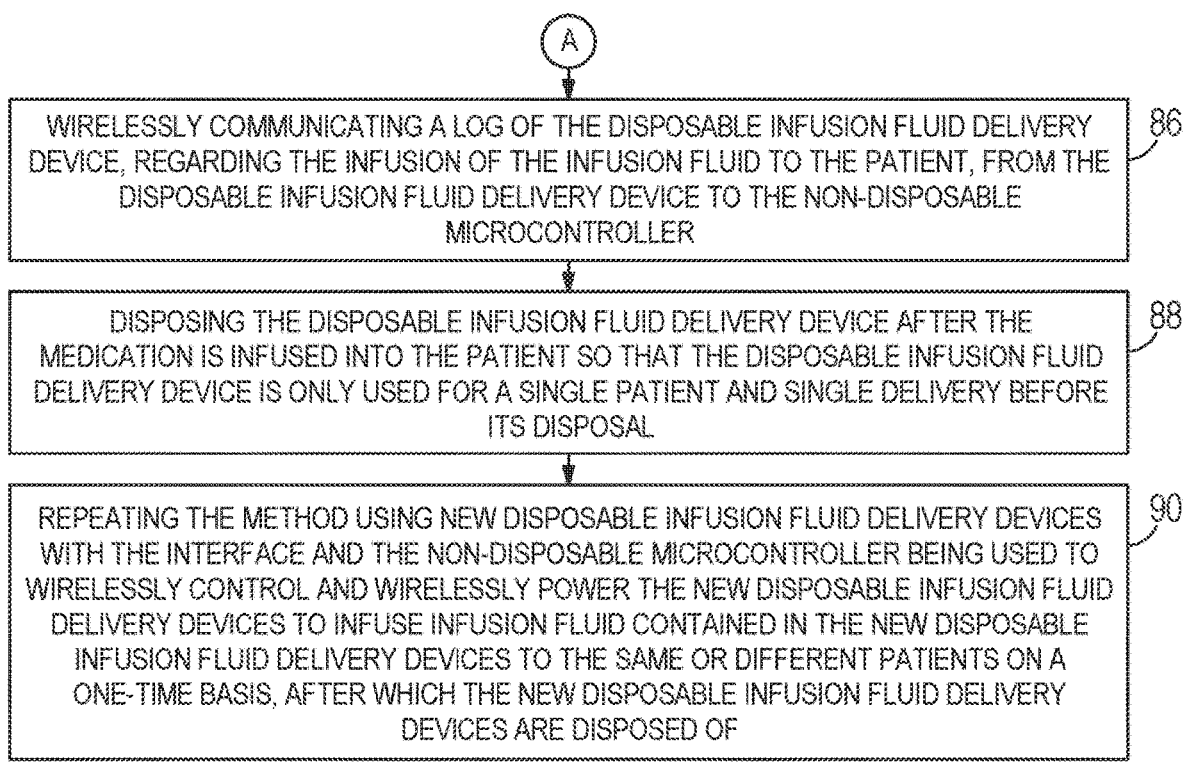

FIG. 6 illustrates a flowchart of one embodiment of a method 70 for delivering infusion fluid to a patient. The method 70 may utilize any of the systems of FIGS. 1-5. In other embodiments, the method may utilize 70 varying systems having differing components and arrangements or configurations. In step 72 a disposable infusion fluid delivery device, comprising at least one disposable infusion container and at least one disposable electronically controlled medication pumping system, is provided. In step 74 a pre-determined amount of infusion fluid for a particular patient is disposed by a drug preparer, such as a pharmacy, into the at least one disposable infusion container according to a prescription the drug preparer received for the particular patient. In step 76 information regarding the infusion fluid, its delivery, or the particular patient to which the medication is to be infused is stored by the drug preparer, who could be a drug manufacturer, compounder or pharmacist, to a barcode or a Radio Frequency Identification Tag attached to the disposable infusion fluid delivery device, to a first memory of a non-disposable microcontroller, to a second memory of the disposable infusion fluid delivery device, or to another memory.

This information may comprise drug lot, program details, patient information, pump lot, pharmacy information, day and time, or other information regarding the patient, the infusion fluid, and/or its delivery. This information may further comprise any combination of the following information: a name or identification of the drug preparer that prepared the infusion fluid contained in the disposable infusion fluid delivery device; a date the infusion fluid was disposed in the disposable infusion fluid delivery device; a date the infusion fluid contained in the disposable infusion fluid delivery device is to expire; a time related to the infusion of the infusion fluid contained in the disposable infusion fluid delivery device; an identification of the infusion fluid contained in the disposable infusion fluid delivery device; a drug identification of the infusion fluid contained in the disposable infusion fluid delivery device; a volume of the infusion fluid contained in the infusion delivery device to be infused into the patient, or a volume of the infusion fluid infused into the patient; a flow rate of the infusion fluid; a delivery time of the infusion fluid; a power status of the interface, of the non-disposable microcontroller, or of the disposable infusion fluid delivery device; a charging status of the interface, of the non-disposable microcontroller, or of the disposable infusion fluid delivery device; an identification or name of the patient; a RX order number; a therapy start time; a therapy end time; a delivery time; one or more alarm conditions; a flow sensor output (flow rate); a pressure sensor output (pressure); an air-in-line sensor output (cumulative air volume); data regarding parameters for infusion of the infusion fluid for the particular patient; or other types of information.

In step 78 the disposable infusion fluid delivery device containing the infusion fluid disposed in the at least one disposable infusion container is delivered from the drug preparer to a location at which the patient is located. In step 80, at the location at which the patient is located, the non-disposable microcontroller, with or without connection to an interface communicates with the disposable infusion fluid delivery device. In step 82 the information of the barcode or the Radio Frequency Identification Tag attached to the disposable infusion fluid delivery device, information contained in the second memory of the disposable infusion fluid delivery device, information contained in the first memory of the non-disposable microcontroller, or other information contained in another memory is wirelessly communicated to and/or read by the non-disposable microcontroller or the disposable infusion fluid delivery device microcontroller as the desired direction of the communication or information flow dictates. In step 84 the disposable electronically controlled medication pumping system of the disposable infusion fluid delivery device is wirelessly controlled and wirelessly powered with the non-disposable microcontroller to infuse the infusion fluid from the disposable infusion container of the disposable infusion fluid delivery device into the patient.

In one embodiment, in step 84 the non-disposable microcontroller wirelessly controls the disposable infusion fluid delivery device to infuse the infusion fluid into the patient utilizing the information of the barcode or the Radio Frequency Tag, utilizing the information saved in the first memory of the non-disposable microcontroller or the second memory of the disposable infusion fluid delivery device, utilizing information saved in another memory, or utilizing other information regarding the infusion fluid, its delivery, or the particular patient to which the infusion fluid is being infused.

In one embodiment, in step 84 any of the interface, the non-disposable microcontroller, and the disposable infusion fluid delivery device may analyze the information provided by the barcode and/or the Radio Frequency Identification Tag, to analyze information stored in the first memory or the second memory regarding the infusion fluid, its delivery, or the particular patient, to analyze information sensed by the temperature sensor, the pressure detection sensor, the flow detection sensor, or the air detection sensor, or to analyze other information provided from other sources regarding the infusion fluid, its delivery, or the particular patient in order to ensure that patient, infusion fluid conditions such as age, storage/transit/delivery temperature, and the like, and infusion delivery parameters are met.

For instance this may include ensuring that the temperature range requirements for the infusion fluid have been followed during storage, shipment and delivery, ensuring that the infusion fluid is being infused into the right patient, ensuring that the infusion fluid is infused using the correct parameters (i.e. time, flow-rate, pressure, air-prevention, temperature, amount delivered, etc.), ensuring that the disposable infusion fluid device is not reused after it has been used on the intended patient, or ensuring that other patient and/or infusion delivery parameters are followed. If the interface, the non-disposable microcontroller, or the disposable infusion fluid delivery device determine that the appropriate patient and/or infusion delivery parameters are not being followed they may be configured to adjust the infusion delivery to ensure compliance with these restraints, provide an alert or alarm signal, and/or to stop the infusion.

In step 86 a log of the disposable infusion fluid delivery device, regarding the infusion of the infusion fluid to the patient, is wirelessly communicated from the disposable infusion fluid delivery device to the non-disposable microcontroller. In step 88 the disposable infusion fluid delivery device is disposed of after the medication is infused into the patient so that the disposable infusion fluid delivery device is only used for a single patient and single delivery before its disposal.

In step 90 the method is repeated using new disposable infusion fluid delivery devices with the interface and the non-disposable microcontroller being used to wirelessly control and wirelessly power the new disposable infusion fluid delivery devices to infuse infusion fluid contained in the new disposable infusion fluid delivery devices to the same or different patients on a one-time basis, after which the new disposable infusion fluid delivery devices are disposed of. Since the interface and the non-disposable microcontroller never came into contact with the disposable infusion fluid delivery device, the infusion fluid itself, or the bodily fluids of patients, no sterilization of the interface or the non-disposable microcontroller is necessary.

In one embodiment, an additional step of the method 70 may comprise a multiplexer of the non-disposable microcontroller concurrently electronically and wirelessly controlling a plurality of disposable infusion fluid delivery devices, each comprising at least one disposable infusion container and a disposable electronically controlled medication pumping system, to deliver different infusion fluids to the patient or to provide a redundant system.

In another embodiment suggested in view of FIGS. 4-6, an additional step of the method 70 may comprise a multiplexer of the non-disposable microcontroller electronically and wirelessly controlling an integrated disposable infusion fluid delivery device having a plurality of electronically controlled medication pumping systems, each being fluidly connected to the same disposable infusion container, to deliver an infusion fluid to the patient in a series or parallel arrangement over time to provide an increased volume or increased volumetric flow rate than would be possible with a single micropump.

In one embodiment, the interface utilized in the method 70 comprises a smartphone, a laptop, a stand-alone computer, a nurse station, an infusion pump, or another type of device. In one embodiment, the non-disposable microcontroller utilized in the method 70 comprises a first microprocessor, a first memory in electronic communication with the first microprocessor, a battery, a power transmitter configured to wirelessly transmit power, and a first wireless communication device. In one embodiment, the disposable electronically controlled medication pumping system of the disposable infusion fluid delivery device utilized in the method 70 comprises a second microprocessor, a second memory in electronic communication with the second microprocessor, a power receiver configured to wirelessly receive power from the power transmitter, a second wireless communication device configured to wirelessly communicate with the first wireless communication device, an infusion channel, a disposable electronically controlled micropump, and valves connected to the infusion channel.

In other embodiments, the interface, the non-disposable microcontroller, and the disposable infusion fluid delivery device may vary. In still other embodiments, any of the steps of the method 70 may be eliminated or changed in substance or in order, or one or more additional steps may be added in varying orders.

The systems and methods of the disclosure provide many benefits over existing infusion systems. For instance, substantial cost is saved in the manufacture of the infusion systems of the disclosure due to the use of the inexpensive disposable electronically controlled micropump which requires a fraction of the power required to run current infusion systems. Moreover, since the disposable infusion fluid delivery devices of the disclosure are sealed, delivered in a sterilized state, and only used once for a single patient and then disposed of, cleaning cost are effectively eliminated and the risk to medical personnel from being exposed to the infusion fluid is similarly substantially eliminated. Additionally, the infusion systems of the disclosure are substantially smaller in weight and size than current infusion systems. These factors reduce shipping and storage cost, and make the infusion system easier to handle and interface with. Further, the infusion systems of the disclosure have significant noise reduction over current infusion systems due to the small disposable micropumps.

Moreover, the small size of the disposable infusion fluid delivery devices of the disclosure reduces the risk of overexposure to the infusion fluid. Smaller and more concentrated amounts of the costly infusion fluids can be delivered.

Additionally, the infusion systems of the disclosure utilize a multiplexed controller which allows multiple drug infusions simultaneously. Further, the disposable infusion fluid delivery devices of the disclosure can be shipped for medical control, i.e. insulin and glucose, in a single pumping mechanism. The infusion systems of the disclosure cover all therapies given via current technology and many others including: blood clotting (heparin and coagulant); blood pressure and heart rate control; oxygenation, SPO2 (saturation of peripheral oxygen); renal failure prevention (protect kidney); fluid volume balance; PCA (patient controlled analgesia)/cardiac arrest; and others. Additionally, the infusion systems of the disclosure provide for automatic data capture, recording, and near real-time feedback regarding the infusion delivery and the patient to ensure that the required parameters for the infusion are met in order to improve reliability and accuracy. Additionally, the infusion system allows configuration of highly redundant medication delivery system, which is impractical or very difficult to achieve using current pump technology.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. A method for delivering infusion fluid to a patient comprising:
   providing a disposable infusion fluid delivery device comprising a single disposable infusion container and a plurality of disposable electronically controlled medication pumping systems;
   disposing a pre-determined amount of the infusion fluid into the single disposable infusion container;
   delivering the disposable infusion fluid delivery device containing the infusion fluid in the single disposable infusion container to a location at which the patient is located;
   wirelessly controlling and wirelessly powering each of the plurality of disposable electronically controlled medication pumping systems of the disposable infusion fluid delivery device with a nondisposable microcontroller to infuse the infusion fluid from the single disposable infusion container of the disposable infusion fluid delivery device, through infusion channels arranged in parallel of the plurality of disposable electronically controlled medication pumping systems, through a connector joined downstream of the infusion channels arranged in parallel of the plurality of disposable electronically controlled medication pumping systems, into the patient; and disposing of the disposable infusion fluid delivery device after the infusion fluid is infused into the patient so that the disposable infusion fluid delivery device is only used for a single patient before disposal.

2. The method of claim 1 further comprising storing information regarding the infusion fluid, a delivery of the infusion fluid, or a particular patient to which the infusion fluid is to be infused to a barcode or a Radio Frequency Identification Tag attached to the disposable infusion fluid delivery device, and wirelessly communicating the information of the barcode or the Radio Frequency Identification Tag attached to the disposable infusion fluid delivery device to the nondisposable microcontroller.

3. The method of claim 2, further comprising sensing conditions of the infusion fluid comprising a temperature of the infusion fluid, a pressure of the infusion fluid, a flow rate of the infusion fluid, or a quantity of air in the infusion fluid.

4. The method of claim 3, further comprising:
analyzing the information provided by the barcode or the Radio Frequency Identification Tag; and
comparing the information provided by the barcode or the Radio Frequency Identification Tag to the conditions of the infusion fluid.

5. The method of claim 4, further comprising:
determining the conditions of the infusion fluid do not comply with the information provided by the barcode or the Radio Frequency Identification Tag.

6. The method of claim 5, further comprising providing an alert or an alarm signal subsequent to determining that the conditions of the infusion fluid do not comply with the information provided by the barcode or the Radio Frequency Identification Tag.

7. The method of claim 5, further comprising stopping delivery of the infusion fluid subsequent to determining that the conditions of the infusion fluid do not comply with the information provided by the barcode or the Radio Frequency Identification Tag.

8. The method of claim 1 further comprising wirelessly communicating a log of the disposable infusion fluid delivery device, regarding the infusion of the infusion fluid to the patient, from the disposable infusion fluid delivery device to the nondisposable microcontroller prior to disposing of the disposable infusion fluid delivery device.

9. The method of claim 1 wherein the nondisposable microcontroller comprises: a first microprocessor, a first memory in electronic communication with the first microprocessor, a battery or an A/C power source, a power transmitter configured to wirelessly transmit power, and a first wireless communication device; and the plurality of disposable electronically controlled medication pumping systems of the disposable infusion fluid delivery device each comprises: a second microprocessor, a second memory in electronic communication with the second microprocessor, a power receiver configured to wirelessly receive the power from the power transmitter, a second wireless communication device configured to wirelessly communicate with the first wireless communication device, a disposable electronically controlled micropump, and valves connected to the infusion channel of each of the plurality of disposable electronically controlled medication pumping systems.

10. The method of claim 9, further comprising pumping the infusion fluid through the infusion channels with the micropump of each of the plurality of disposable electronically controlled medication pumping systems.

11. The method of claim 9, further comprising controlling a flow of the infusion fluid with the valves of each of the plurality of disposable electronically controlled medication pumping systems.

12. The method of claim 1, wherein each of the plurality of disposable electronically controlled medication pumping systems is permanently hermetically sealed to the single disposable infusion container by at least one seal or gasket.

13. The method of claim 1, further comprising operating the plurality of disposable electronically controlled medication pumping systems in parallel to pump the infusion fluid concurrently from the single disposable infusion container at a combined flow rate.

14. The method of claim 13, wherein the combined flow rate is between 0.1 to 2,000 milliliters of the infusion fluid per hour.

15. The method of claim 1, further comprising receiving an input on an interface to communicate with the nondisposable microcontroller.

16. The method of claim 15, wherein the interface comprises a smartphone, a tablet, a laptop, a stand-alone computer, a nurse station, or an infusion pump.

17. The method of claim 1, further comprising sensing a temperature of the infusion fluid, a pressure of the infusion fluid, a flow rate of the infusion fluid, or a quantity of air in the infusion fluid.

18. The method of claim 1, further comprising repeating using the nondisposable microcontroller with a second disposable infusion fluid delivery device.

19. The method of claim 1, further comprising concurrently electronically and wirelessly controlling a plurality of disposable infusion fluid delivery devices including the disposable infusion fluid delivery device with a multiplexer of the nondisposable microcontroller.

20. The method of claim 19, further comprising delivering different infusion fluids including the infusion fluid to the patient with the plurality of disposable infusion fluid delivery devices.

* * * * *